United States Patent
Patil et al.

(10) Patent No.: US 12,059,539 B2
(45) Date of Patent: Aug. 13, 2024

(54) GUIDEWIRE ASSEMBLY AND METHOD OF MAKING

(71) Applicant: PATHWAYS MEDICAL CORPORATION, Santa Clara, CA (US)

(72) Inventors: Nitin Patil, Danville, CA (US); Philip R. Houle, Sunnyvale, CA (US)

(73) Assignee: PATHWAYS MEDICAL CORPORATION, Santa Clara, CA (US)

( * ) Notice: Subject to any disclaimer, the term of this patent is extended or adjusted under 35 U.S.C. 154(b) by 0 days.

(21) Appl. No.: 18/236,076

(22) Filed: Aug. 21, 2023

(65) Prior Publication Data

US 2023/0390534 A1    Dec. 7, 2023

Related U.S. Application Data

(63) Continuation of application No. 17/646,270, filed on Dec. 28, 2021, now Pat. No. 11,771,872, which is a
(Continued)

(51) Int. Cl.
| | |
|---|---|
| A61M 25/00 | (2006.01) |
| A61B 5/00 | (2006.01) |
| A61B 5/021 | (2006.01) |
| A61B 5/0215 | (2006.01) |
| A61B 5/027 | (2006.01) |
| A61B 5/107 | (2006.01) |

(Continued)

(52) U.S. Cl.
CPC ............. *A61M 25/09* (2013.01); *A61B 5/021* (2013.01); *A61B 5/0215* (2013.01); *A61B 5/027* (2013.01); *A61B 5/1076* (2013.01); *A61B 5/287* (2021.01); *A61B 5/6851* (2013.01); *A61B 2562/0247* (2013.01); *A61B 2562/12* (2013.01); *A61M 2025/0002* (2013.01); *A61M 2025/09075* (2013.01); *A61M 2025/09083* (2013.01); *A61M 2025/09108* (2013.01)

(58) Field of Classification Search
CPC ....... A61B 5/021; A61B 5/0215; A61B 5/027; A61B 5/1076; A61B 5/287; A61B 5/6851; A61B 2562/0247; A61B 2562/12; A61M 25/09; A61M 2025/0002; A61M 2025/09075; A61M 2025/09083; A61M 2025/09108
See application file for complete search history.

(56) References Cited

U.S. PATENT DOCUMENTS

| | | |
|---|---|---|
| 5,448,020 A | 9/1995 | Pendse |
| 5,768,776 A | 6/1998 | Pendse |
| (Continued) | | |

FOREIGN PATENT DOCUMENTS

| | | |
|---|---|---|
| JP | H07-211995 A | 8/1995 |
| JP | 2004-146836 A | 5/2004 |
| (Continued) | | |

*Primary Examiner* — Paul D Kim
(74) *Attorney, Agent, or Firm* — Oliff PLC

(57) ABSTRACT

Guidewires having conductive elements are described where in one variation, the guidewire may be formed by disposing an insulative layer upon a surface of the guidewire core, and printing one or more conductive traces directly upon a surface of the insulative layer.

8 Claims, 36 Drawing Sheets

Related U.S. Application Data continuation of application No. 15/654,450, filed on Jul. 19, 2017, now Pat. No. 11,324,929.

(60) Provisional application No. 62/363,987, filed on Jul. 19, 2016, provisional application No. 62/363,992, filed on Jul. 19, 2016, provisional application No. 62/419,090, filed on Nov. 8, 2016.

(51) Int. Cl.
*A61B 5/287* (2021.01)
*A61M 25/09* (2006.01)

(56) References Cited

U.S. PATENT DOCUMENTS

| | | |
|---|---|---|
| 5,931,819 A | 8/1999 | Fariabi |
| 5,947,905 A | 9/1999 | Hadjicostis et al. |
| 6,090,052 A | 7/2000 | Akerfeldt et al. |
| 6,106,486 A | 8/2000 | Tenerz et al. |
| 6,287,292 B1 | 9/2001 | Fariabi |
| 6,623,418 B2 | 9/2003 | Smith |
| 8,239,003 B2 | 8/2012 | Akins |
| 8,858,468 B2 | 10/2014 | Sela et al. |
| 9,387,323 B2 | 7/2016 | Fleischhacker et al. |
| 9,446,219 B2 | 9/2016 | Lupton |
| 2004/0080052 A1 | 4/2004 | Ou et al. |
| 2009/0112128 A1 | 4/2009 | Schiff et al. |
| 2013/0237864 A1 | 9/2013 | Mazar et al. |
| 2013/0274591 A1 | 10/2013 | Sonmez et al. |
| 2013/0274619 A1 | 10/2013 | Stone et al. |
| 2014/0183381 A1 | 7/2014 | Carbaugh et al. |
| 2014/0187874 A1 | 7/2014 | Burkett et al. |
| 2014/0209372 A1 | 7/2014 | Sobe |
| 2014/0236126 A1 | 8/2014 | Lupton |
| 2015/0074995 A1 | 3/2015 | Patil et al. |
| 2016/0249817 A1 | 9/2016 | Mazar et al. |
| 2016/0338647 A1 | 11/2016 | Sterrett et al. |
| 2018/0093078 A1 | 4/2018 | Patil et al. |
| 2019/0183355 A1 | 6/2019 | Dutta et al. |
| 2021/0030364 A1 | 2/2021 | Burkett et al. |
| 2022/0111182 A1* | 4/2022 | Patil .................... A61B 5/6851 |
| 2022/0181827 A1* | 6/2022 | Patil .................... A61B 5/6851 |

FOREIGN PATENT DOCUMENTS

| | | |
|---|---|---|
| JP | 2015-519124 A | 7/2015 |
| JP | 2016-509497 A | 3/2016 |
| WO | 2013/169492 A1 | 11/2013 |
| WO | 2015/116692 A1 | 8/2015 |
| WO | 2018/017731 A1 | 1/2018 |

* cited by examiner

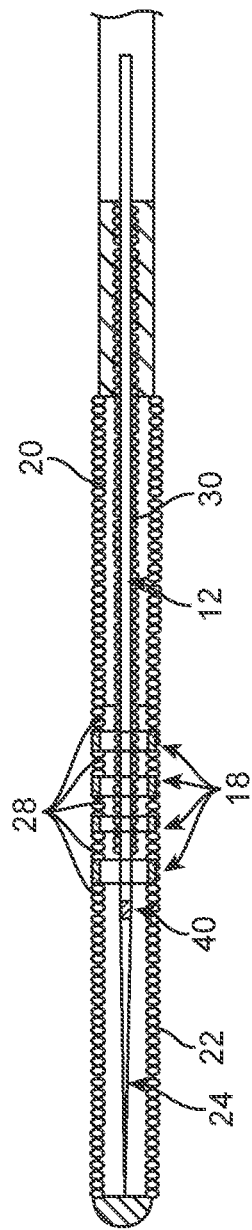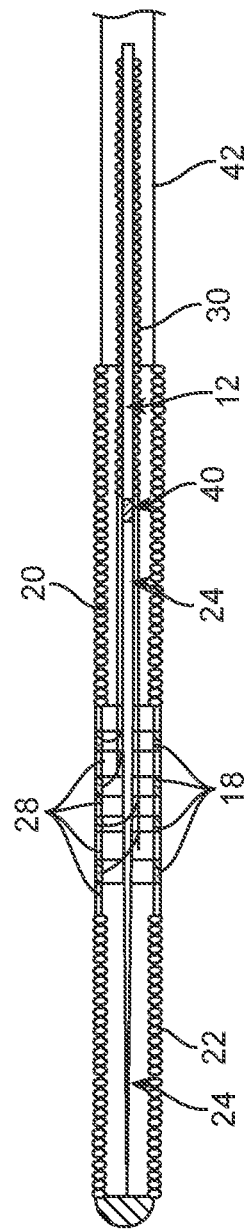

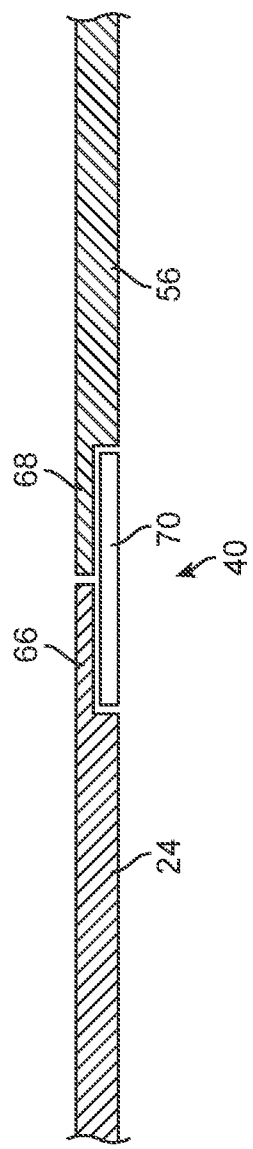

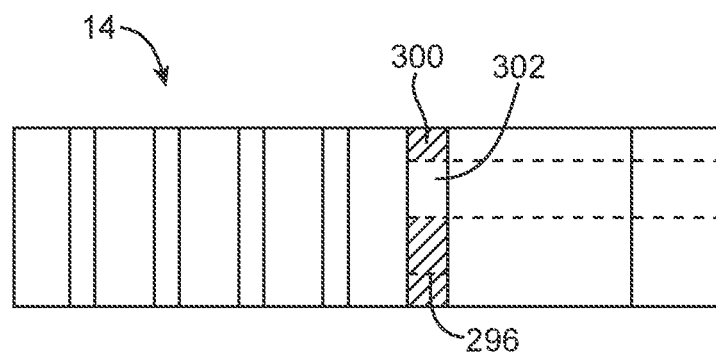
FIG. 26A
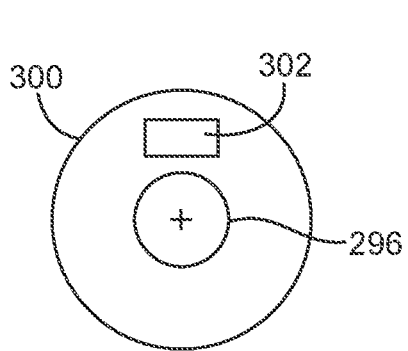 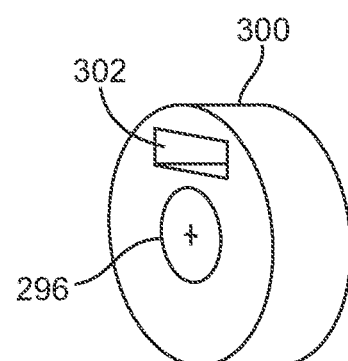
FIG. 26B  FIG. 26C

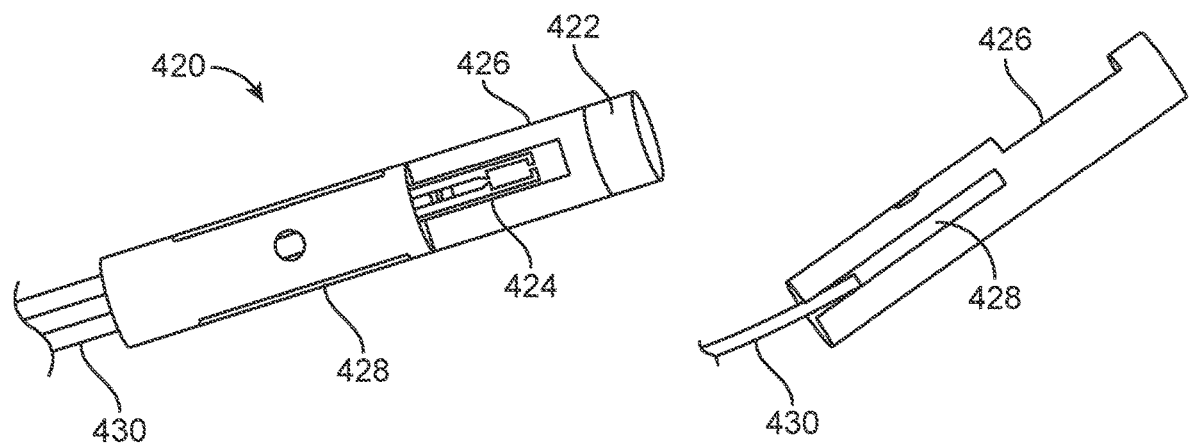
FIG. 33A
FIG. 33B
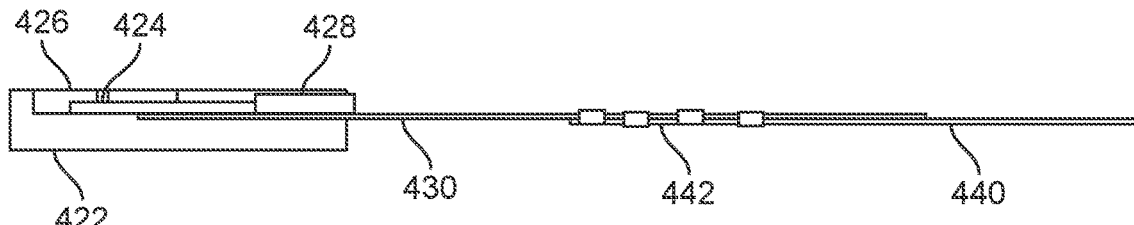
FIG. 34A
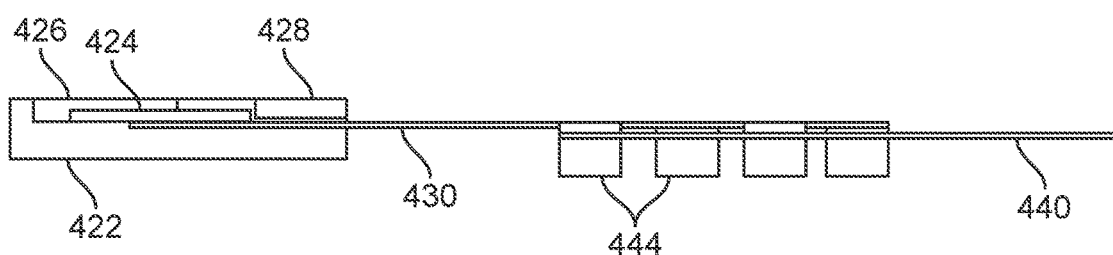
FIG. 34B

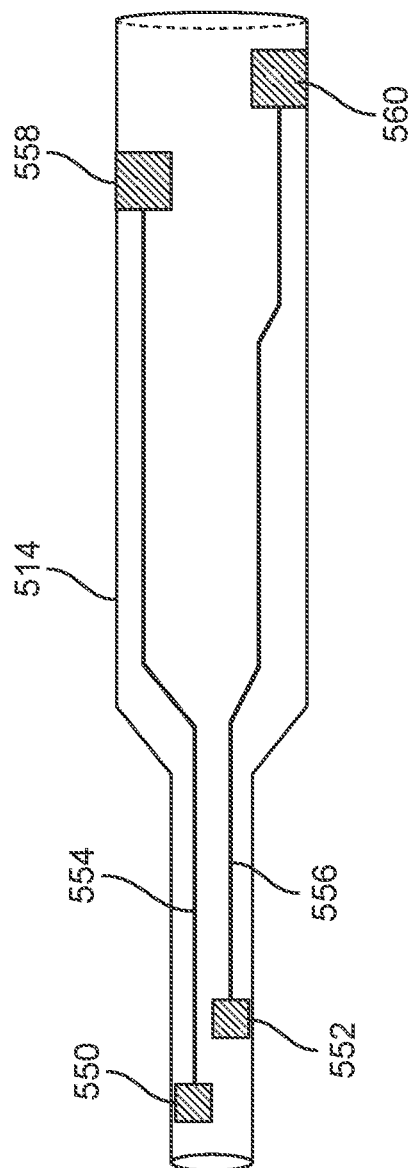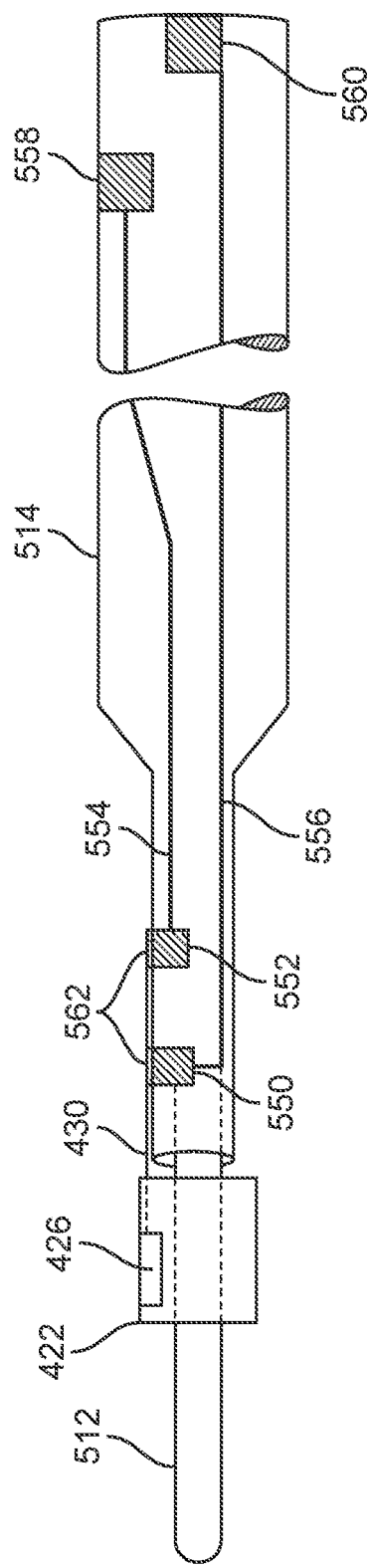
FIG. 42A
FIG. 42B

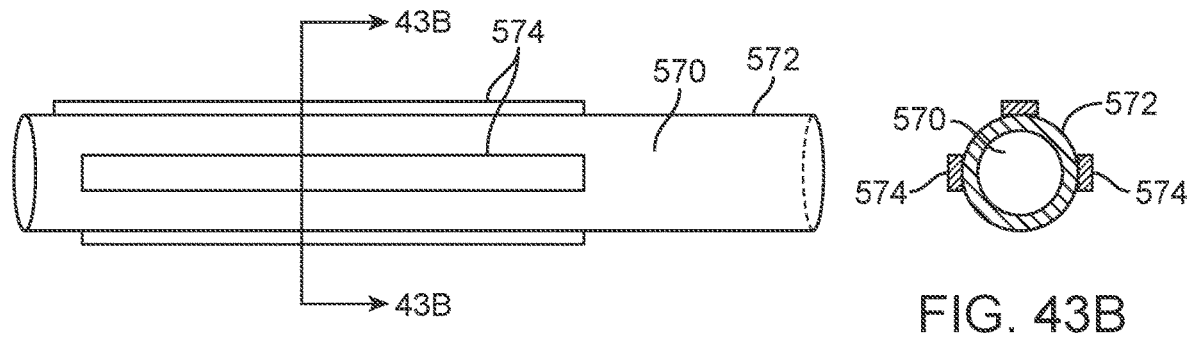
FIG. 43A
FIG. 43B
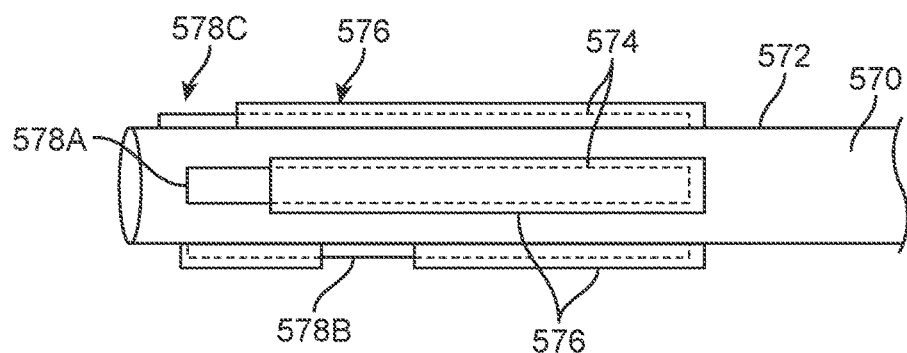
FIG. 43C
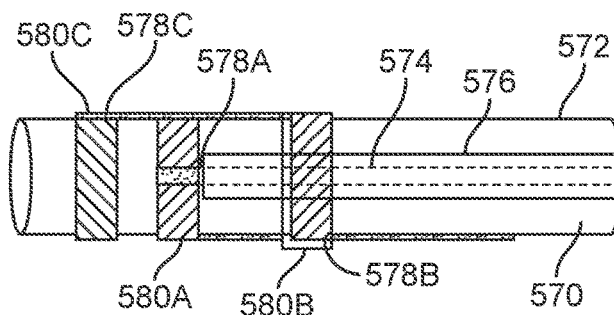
FIG. 43D

GUIDEWIRE ASSEMBLY AND METHOD OF MAKING

CROSS-REFERENCE TO RELATED APPLICATIONS

This application is a continuation of U.S. patent application Ser. No. 17/646,270, filed on Dec. 28, 2021, now U.S. Pat. No. 11,771,872, which is a continuation of U.S. patent application Ser. No. 15/654,450, filed Jul. 19, 2017, now U.S. Pat. No. 11,324,929, which claims the benefit of priority to U.S. Prov. Apps. 62/363,987 filed Jul. 19, 2016; 62/363,992 filed Jul. 19, 2016; and 62/419,090 filed Nov. 8, 2016, each of which is incorporated herein by reference in its entirety.

FIELD OF THE INVENTION

The present invention relates to methods and apparatus for the assembly of guidewires having multiple sensors incorporated within or along the body of the guidewire. In particular, the present invention relates to methods and apparatus for the assembly of guidewires incorporating pressure sensor within or along the body of the guidewire.

BACKGROUND OF THE INVENTION

Guidewires may have a number of sensors or sensor assemblies integrated directly into the guidewire. Such sensor-equipped guidewires may be adapted for measuring various physiological parameters within a patient's body. For instance, sensors typically have one or more cables passed through the guidewire for electrically coupling the sensor element to an electronic assembly.

Guidewires are generally comprised of a hypotube and coiled segment about a core wire which may extend through the length or a partial length of the guidewire. The core wire may be fabricated from stainless steel or Nitinol with the coiled segment fabricated from a wire or braid which provide for flexibility, pushability, and kink resistance to the guidewire. Nitinol wire, used by itself or braided with stainless steel, may further help to increase flexibility and allow the wire to spring back into shape.

Moreover, guidewires have a standard diameter of 0.014 in. and consequently accommodating certain types of sensors or having multiple sensors may be limited by the relatively small space provided by the guidewire. Moreover, guidewires are typically used for insertion into and advancement through the vasculature which can present an extremely tortuous pathway. Thus, the guidewire and any sensors or electrodes along the guidewire may experience relatively large stresses as the guidewire is pushed, pulled, or torqued over a passageway having numerous curves and bends.

Guidewires incorporating one or more electrodes along their length may present additional challenges to guidewire construction and use. For instance, the presence of a plurality of electrodes along the guidewire may require additional conductive wiring passed through the length of the guidewire. Because of the limited space and flexibility required from guidewires, any sensors and/or electrodes positioned along their length are desirably correspondingly constructed.

Consequently, there is a need for guidewire designs which provide for effective construction of a guidewire incorporating one or more electrodes and/or sensors along the length.

SUMMARY OF THE INVENTION

Guidewires may incorporate a number of different sensors within or along the body of the guidewire. One particular variation may incorporate a pressure sensor optionally with one or more electrodes along the body of the guidewire or at the distal end of the guidewire. A guidewire having one or more electrodes integrated directly along the guidewire body may have a proximal coil attached to an electrode assembly having one or more electrodes and a distal coil attached to a distal end of the electrode assembly. A core wire may extend through the length of the guidewire assembly and may extend partially or entirely through the electrode assembly.

One variation for assembling the guidewire assembly may generally comprise providing a core wire having a tapered distal section, securing a sensor package having one or more conductive wires to the core wire by passing the core wire through a wire receiving channel defined through or along the sensor package, securing the one or more conductive wires to the core wire, and then encasing the one or more conductive wires and the core wire.

One example of a method of forming a guidewire assembly may generally comprise providing a guidewire core, disposing an insulative layer upon a surface of the guidewire core, and printing one or more conductive traces directly upon a surface of the insulative layer.

Another example of a method of forming a guidewire assembly may generally comprise providing a guidewire core, disposing an insulative layer upon a surface of the guidewire core, and disposing an aerosolized conductive ink upon a surface of the insulative layer to form one or more conductive traces.

Yet another example of a method of forming a guidewire assembly may generally comprise providing a guidewire core, disposing an insulative layer upon a surface of the guidewire core, disposing a conductive layer upon a surface of the insulative layer, and removing portions of the conductive layer such that one or more conductive traces are formed upon the insulative layer.

In forming the guidewire assembly, the pressure sensor packaging, in one variation, may generally comprise a sensor casing which may form a cylindrically shaped housing which encloses or supports the components of the pressure sensor secured within. The sensor casing may define a sensing window along a side surface of the casing which exposes the pressure sensor within to the fluid environment. A sensor core may be secured within and along the sensor casing which connects to a flex circuit which may extend from from a proximal end of the sensor casing for connection to a controller or processor via one or more conductors extending through the guidewire length. The conductive traces or wires along the flex circuit may be attached directly to one or more corresponding conducting wires which may extend proximally through the guidewire body for electrical connection to a controller or processor.

Another variation includes a configuration where the flex circuit extends proximally from the sensor casing but instead of being directly attached to the one or more conducting wires, the flex circuit may be electrically connected to one or more conducting ring elements which in turn are electrically connected to the one or more conducting wires. The ring elements may be aligned coaxially and adjacent to one another and the number of elements used may depend upon the number of electrical connections desired. The one or more conducting wires may be selectively coupled electrically to a particular pad or trace on the flex circuit so that each ring element is electrically connected to a single pad or trace. Each ring element may then be electrically coupled to a selective conducting wire along an inner diameter of the ring element leaving the remainder of the ring element available for electrical connection to another conductor or component, if so desired.

The sensor casing may define a longitudinal passageway through the entire casing to allow for passage of a guidewire core therethrough. The casing may further define a distal opening into which a guidewire tip may be positioned and secured to extend from the distal end of the casing with the guidewire core extending longitudinally through the casing adjacent or beneath the flex circuit, pressure sensor, and sensing window. The sensor core is shown secured within the casing adjacent to the flex circuit which extends proximally from the casing.

In yet another variation for electrically coupling elements within or along a guidewire, a guidewire assembly may have conductive ink printed upon a polymer substrate to form a subassembly for carrying signals from one end to the other end of the guidewire or catheter. Using conductive traces directly upon the device substrate and then insulating the traces by a dielectric material eliminates the need to have conducting wires and associated processing and handling of the same.

A polymer layer (e.g., PET, PTFE, etc.) may be coated over the guidewire core such as via heat shrink to provide an insulating substrate. The polymer layer may be coated or laid upon the entirety of the guidewire core or a portion of the distal end may remain uncoated for securement of the pressure sensor assembly. The one or more conductive traces (e.g., nano silver, nano gold, nano copper, etc.) may then be printed directly upon the polymer layer such that the traces extend from one or more corresponding distal pads to one or more corresponding proximal pads.

Because these one or more conductive traces are printed directly upon the polymer layer, they may be configured in a number of different patterns. Once the one or more conductive traces have been printed upon the polymer layer, the traces may then be insulated. One variation for insulating the traces may involve masking the ends of the traces that will need to remain exposed to form pads for electrical connections and then depositing another layer of polymer upon the conductive traces. For instance, another heat shrink tubing or layer may be used or another layer of polymer (such as PTFE, paralyne, etc.) may be deposited upon the exposed conductive traces using, e.g., physical vapor deposition, dip coating, etc.).

In yet another variation, a conductive coating can be applied over the dielectric coating either by a bulk metallization process such as physical vapor deposition (PVD), or by electro plating, electroless plating, printing a wider metal layer using conductive inks on top of the dielectric layer, etc. Such a metal layer can provide EM shielding and thus eliminate or reduce noise and increase system signal to noise ratio (SNR).

Another variation for insulating the traces may involve printing a dielectric polymer directly upon the conductive traces using polymer inks. In the case of using polymer inks to directly print upon the conductive traces, the printing process may be used to selectively print the polymer ink to create the insulating layer while exposing portions of the conductive traces to form conductive pads for electrical coupling to components.

Regardless of which method is used, the resulting guidewire core and polymer layer may be coupled with the pressure sensor assembly. The one or more ring elements may be electrically coupled along portions of their inner diameter to a corresponding pad exposed along the flex circuit and a second portion along the one or more ring elements may be electrically coupled to a corresponding pad of the conductive traces disposed upon the polymer layer to electrically couple the pressure sensor assembly (or any other component). The distal coil tip may then be attached to the distal end of the sensor casing and the polymers may be reflowed or molded over the guidewire core along the central section, the distal coil or tip along the distal section, and the remainder of the guidewire core along the proximal section as well as the portions between the electrodes (if utilized).

Another variation of the assembly method includes the polymer layer formed separately prior to being disposed upon the guidewire core. The conductive traces may be printed directly upon the outer layer of the polymer along with their corresponding exposed pads extending over the length of the polymer layer. The insulative layer may be likewise printed directly upon the conductive traces. With the pre-printed polymer layer, the guidewire core may be inserted into the polymer layer and bonded with any number of suitable adhesives, e.g., cyanoacrylate, etc. The pressure sensor assembly may then be secured to the guidewire core and the flex circuit may be electrically coupled directly to the exposed pads at attachments to complete the electrical connection. In yet another variation for printing conductive traces, a polymer tube may be disposed upon a guidewire core and one or more conductive traces may be printed upon the outer layer of the tube. Conductive ink may then be used to print circular rings upon the polymer tube such that a ring coincides with an exposed region of the conductive traces so that the pressure sensor assembly flex circuit, or any other component, may be electrically coupled to the conductive traces via connection to the circular rings. Because the circular rings are printed circumferentially around the tube, the exposed regions may be off set longitudinally from one another to allow for the ring to be printed around the entire tube circumference. Also, there is preferably adequate longitudinal spacing between the exposed regions to allow for the rings to be printed coaxially relative to one another without interference. In other variations, partial circumferential rings may be printed than full circumferential rings.

Yet another variation for creating conductive traces may have a first insulative polymer layer (e.g., PARYLENE (Specialty Coating Systems, Inc., Indianapolis, IN), TEFLON (E. I. Du Pont De Nemours, Wilmington, DE), polyimide, etc.) disposed upon an outer surface of the guidewire core. A second conductive polymer layer (gold, silver, copper, etc.) having a conductive material may then be coated upon the first polymer layer using any number of processes such as, e.g., electroless deposition, physical vapor deposition, etc. The thickness of the conducting layer is dependent on the application and is often determined considering both electrical requirements (current carrying capacity) and mechanical requirements of the device (e.g. stiffness). This second conductive layer may be separated into discrete conductive elements using, e.g., laser micro machining, photochemical etching, etc.

The entire assembly can then be insulated using dielectric insulative polymer either in the form of a coating or heat shrink (e.g. Teflon, PET, etc.) depending on the application. Depending on the application several discrete conducting elements can be formed. Also depending on the application various connecting terminal size and shapes can be formed at either ends to facilitate connecting to the discrete conducting elements so formed. Such a construction technique helps achieve several discrete conducting elements directly on the device thereby eliminating the need to remove material to accommodate separate conducing wires or make the device hollow to accommodate conducting wires or elements. Therefore, the intended device performance is greatly enhanced and manufacturing costs are reduced.

BRIEF DESCRIPTION OF THE DRAWINGS

FIG. 3 shows a side view of an electrode assembly having one or more electrodes spaced apart from one another with insulative material positioned between.

FIG. 5 shows a cross-sectional side view of another variation for assembling a guidewire having one or more electrodes positioned therealong.

FIG. 6 shows a cross-sectional side view of yet another variation for assembling a guidewire having one or more electrodes.

FIG. 7E shows a cross-sectional side view of a core wire to hypotube attachment using a clip or collar for coupling the two portions.

FIGS. 26A to 26C show side, end, and perspective views of another variation of a barrier segment which may be integrated into the guidewire.

FIGS. 33A and 33B show perspective and side views of a one variation of a pressure sensor packaging.

FIG. 34A shows a side view of one variation of a configuration for electrically connecting the sensor casing components to one or more conducting wires.

FIG. 34B shows a side view of another variation in which the flex circuit extends proximally from the sensor casing and is electrically connected to one or more conducting ring elements which in turn are electrically connected to the one or more conducting wires.

FIGS. 42A and 42B show side views of the polymer layer formed separately prior to being disposed upon the guidewire core.

FIGS. 43A to 43D show a variation in which a polymer tube may be disposed upon a guidewire core and one or more conductive traces are printed upon the outer layer of the tube.

DETAILED DESCRIPTION OF THE INVENTION

Figure 1:
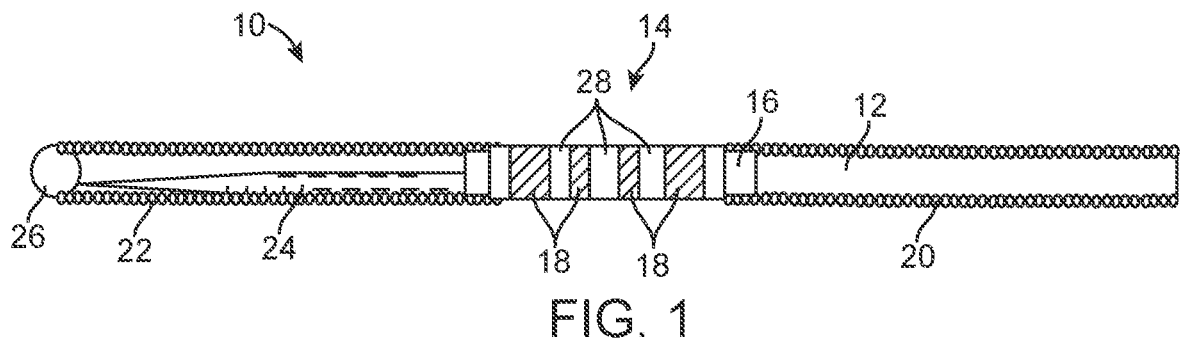
FIG. 1 shows a cross-sectional side view of one variation of a guidewire illustrating one or more electrodes positioned along the guidewire body near or at the distal end.

Guidewires may incorporate a number of different sensors within or along the body of the guidewire. One particular variation may incorporate a pressure sensor with one or more electrodes along the body of the guidewire or at the distal end of the guidewire. To achieve the combination of the pressure sensor and one or more electrodes, various assembly methods and apparatus may be utilized as described in further detail herein.

Revascularization of vessels having greater than 70% stenosis is supported by data confirming the efficacy of both percutaneous and surgical methods of revascularization to treat angina pectoris. However, this decision is not obvious when it comes to a decision to re-vascularize intermediate lesions, e.g., 30% to 70% stenosis. A functional assessment of the stenosis can help to guide such decision. Fractional Flow Reserve (FFR) which is a ratio of pressure distal to the stenosis at maximal hyperemia (maximum physiologic flow) to the aortic pressure (Ao) is a clinical parameter used to determine functional significance of a lesion. The FFR is a fractional value that indicates how much the flow of blood to the vasculature of the myocardium through the blood vessel is compromised due to the stenosis. A value close to 1 indicates very little compromise while decreasing values indicate increasing compromise. A threshold of ischemia exists for FFR that allows the discrimination of functionally significant lesions. A FFR of below 0.75 is almost always associated with inducible ischemia. The randomised FAME trial (NEJM, 2009) showed that FFR-guided coronary intervention resulted in a significant reduction in coronary events and improved survival compared to simple angiographically-guided intervention.

Today there are several product solutions that provide FFR in a clinical setting. The disposable element that measures intravascular pressure is either guidewire based, e.g., CERTUS PRESSURE WIRE (St. Jude Medical, St. Paul MN), PRIMEWIRE (Volcano Corp., Rancho Cordova, CA) or catheter based, e.g. ASCIST (St. Jude Medical). Generally, various types of sensors (pressure sensors, temperature, flow, electrical, etc.) may be mounted or positioned within a guidewire or catheter for measuring intravascular parameters. Particularly, there are various types of pressure sensors that can be mounted to measure intravascular pressure. Due to the small size of the guidewires (typically 0.014 in. diameter) packaging the sensors and associated conducting elements poses a significant challenge. Typically, the measurement circuitry is situated proximally and often outside the patient's body and is connected to the sensors distally using a plurality of signal conducting elements (e.g. wires, optic fibers etc.) that need to be routed through the guidewire. The choice of the conducting elements and routing method can have a profound influence on the mechanical performance of the guidewire. Guidewires need to possess specific mechanical performance characteristics such as trackablity and torquability to allow the physician to steer these devices to desired location in the arteries within a reasonable time. There is a significant push and need to have multifunctional devices that possess and combine various diagnostics into a single device with little compromise to mechanical performance and deliverability.

Examples of guidewires which may incorporate one or more electrodes for assessing various anatomical parameters, such as lumen dimension in vivo, and which may also integrate one or more sensors such as pressure sensors, are shown and described in further detail in the following: U.S. Prov. 61/383,744 filed Sep. 17, 2010; U.S. application Ser. No. 13/159,298 filed Jun. 13, 2011 (U.S. Pub. 2011/0306867); Ser. No. 13/305,610 filed Nov. 28, 2011 (U.S. Pub. 2012/0101355); Ser. No. 13/305,674 filed Nov. 28, 2011 (U.S. Pub. 2012/0101369); Ser. No. 13/305,630 filed Nov. 28, 2011 (U.S. Pub. 2012/0071782); Ser. No. 13/709,311 filed Dec. 10, 2012; Ser. No. 13/764,462 filed Feb. 11, 2013; and Ser. No. 14/535,165 filed Nov. 6, 2014 (U.S. Pub. 2015/0074995). Each of the applications is incorporated herein by reference in its entirety and is provided for any purpose herein.

Additional examples are also shown and described for the assembly and use of the combination of one or more pressure sensors and one or more electrodes within or along a guidewire in PCT/US2012/034557 filed Apr. 20, 2012 (published as WO 2012/173697 and designating the U.S.) which is also incorporated herein by reference in its entirety for any purpose herein. It is intended that any of these guidewires and other guidewires may utilize any of the methods and apparatus described herein in various combinations as practicable.

Turning now to FIG. 1, an example of a guidewire 10, e.g., 0.014 in. diameter guidewire, having one or more electrodes integrated directly along the guidewire body is shown in the partial cross-sectional side view. As shown, a hypotube 12, e.g., Nitinol, stainless steel, etc., may have a proximal coil 20, e.g., fabricated from stainless steel, attached to an electrode assembly 14 having one or more electrodes 18 (in this variation four electrodes spaced apart from one another) and a distal coil 22 attached to a distal end of the electrode assembly 14 and terminating in an atraumatic distal tip 26.

The electrode assembly 14 may further have insulative spacing segments 28 positioned between each of the electrodes 18 to provide for electrical insulation and both the electrodes 18 and spacing segments 28 may be positioned along an electrode assembly or substrate 16 fabricated from, e.g., polyimide. One or both of the proximal coil 20 and/or distal coil 22 may be fabricated from a variety of biocompatible materials which also provide sufficient structural strength, e.g., platinum (Pt), platinum-iridium alloys (Pt/Ir), etc. A core wire 24 may extend through the length of the guidewire assembly 10 and may extend partially or entirely through the electrode assembly 14. The core wire 24 may be fabricated from, e.g., stainless steel, Nitinol, etc., and may also be tapered into a relatively smaller diameter the further distal the core wire 24 extends.

Figure 2:
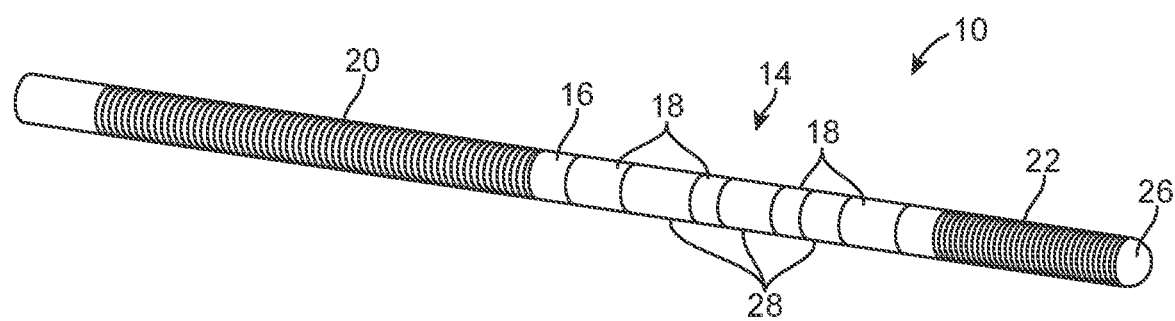
FIG. 2 shows a perspective view of the distal end electrode spacing.
Figure 3:
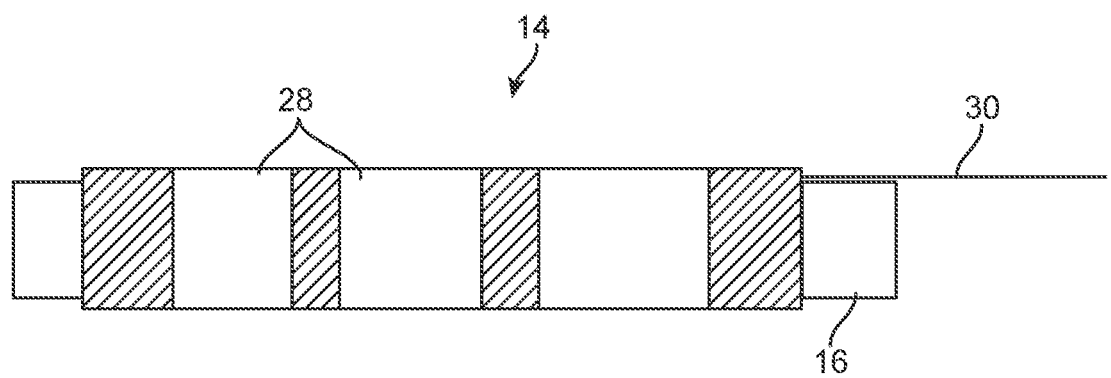

Another view of the guidewire assembly 10 is shown in the perspective view of FIG. 2, which illustrates the spacing of the electrodes 18 with the adjacent insulative spacing segments 28 between each of the electrodes 18. Also shown are the proximal and distal coils 20, 22, respectively, and the smooth outer surface presented by the assembly 10. FIG. 3 shows a side view of the electrode assembly 16 removed from the guidewire body to illustrate the positioning of the electrodes 18 relative to the spacing segments 28 and how the one or more conducting wires 30 electrically coupled to each of the respective electrodes 18 may extend proximally from the assembly 16.

Figure 4A:
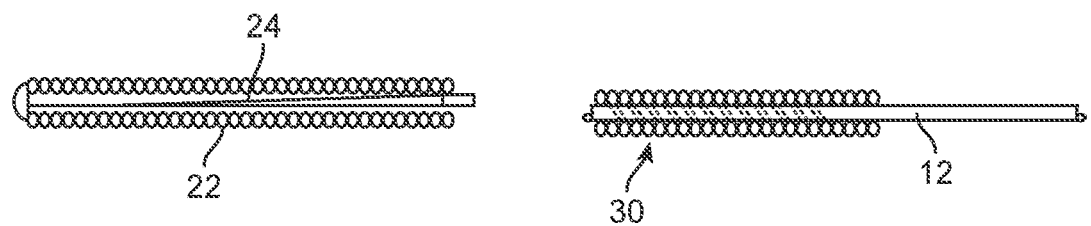
FIGS. 4A to 4C illustrate one variation for assembling an electrode assembly along a guidewire.
Figure 4B:
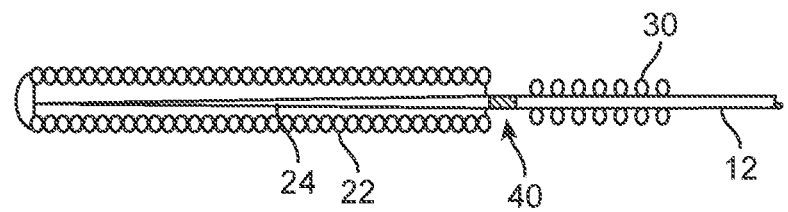
Figure 4C:
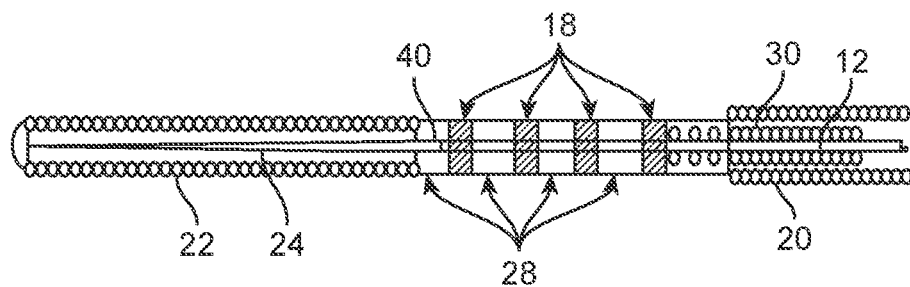

FIGS. 4A to 4C illustrate one variation for assembling the guidewire assembly and integrating an electrode assembly 16. As shown in FIG. 4A, core wire 24 may be secured within a portion of the distal coil 22 where the core wire 24 having an outer diameter of, e.g., 0.005 in., may be tapered to an outer diameter of, e.g., 0.002 in., over a length of, e.g., 3 cm. A core wire or hypotube 12 separate from the core wire 24 may have one or more conducting wires 30 for attachment to the electrodes twisted, spooled, or otherwise wrapped around the core wire or hypotube 12. With this assembly, the proximal end of the core wire 24 and the distal end of core wire or hypotube 12 may be coupled, joined, or otherwise attached at an attachment 40, e.g., laser welded joint, to one another, as shown in the side view of FIG. 4B. In this embodiment two different core wires are described since the materials of the core wires can be different (e.g. Nitinol for the distal core wire and stainless steel for the proximal core wire) to take advantage of the material properties and satisfy different performance requirements of the wire (e.g., high kink resistance offered by a Nitinol distal core versus high stiffness along the proximal shaft which may be derived using a stainless steel core). However, it should be noted that a single continuous core wire material (e.g., stainless steel) may be used for the wire construction.

The electrode assembly having the electrodes 18 and insulative spacing segments 28 may then be advanced over the core wire or hypotube 12 and conducting wires into contact against the proximal end of the distal coil 22 where the electrodes 18 may be electrically coupled to a corresponding conducting wire 30. The proximal coil 20 may be advanced over the core wire or hypotube 12 into contact against the proximal end of the electrode assembly and the two may be coupled or otherwise attached to one another, as shown in the side view of FIG. 4C. It should be noted that in place of a coil 20 a suitable polymer (e.g., polyimide or nylon) can be used to encapsulate the core and the conducting wires through the length of the guidewire.

In yet another variation for manufacturing the guidewire, FIG. 5 shows a partial cross-sectional side view of a guidewire assembly having a relatively shortened core wire 24, e.g., less than 3 cm, such that the proximal end of the core wire 24 is positioned within the distal coil 22. The distal end of core wire or hypotube 12 is correspondingly longer and may extend distally through the electrode assembly and at least partially into and through the proximal end of the distal coil 22. The addition of a hypotube 42, e.g., laser cut, may be attached or coupled to a proximal end of the proximal coil 20.

FIG. 6 shows yet another variation where the core wire 24 may be relatively lengthened such that the core wire 24 has a length greater than 3 cm, e.g., 20 cm or longer, and may extend proximally such that the terminal end is positioned proximally of the electrode assembly and within the proximal coil 20. The attachment 40 between the proximal end of the lengthened core wire 24 and the distal end of the core wire or hypotube 12 may be accordingly positioned proximal to the electrode assembly and within the proximal coil 20 or within the hypotube 42.

FIGS. 7A to 7D illustrate yet another method of attachment to a core wire 24 through an electrode assembly and directly to a hypotube 42. In this variation, the hypotube 42 may have a distal section initially reduced in diameter from an outer diameter of, e.g., 0.014 in., down to an outer diameter of, e.g., 0.012 in., along a length of less than, e.g., 1.0 in., as shown by the reduced annular portion 50 in the side view of FIG. 7A. The reduced annular portion 50 may then be further processed to remove an arcuate or skived portion 54 which extends from a shoulder 58 of the annular portion 50 (e.g., forming a length of 0.315 in.) down to the distal end 52 of the hypotube 42 such that a tapered distal section 56 is formed, as shown in the side view of FIG. 7B.

Figure 7A:
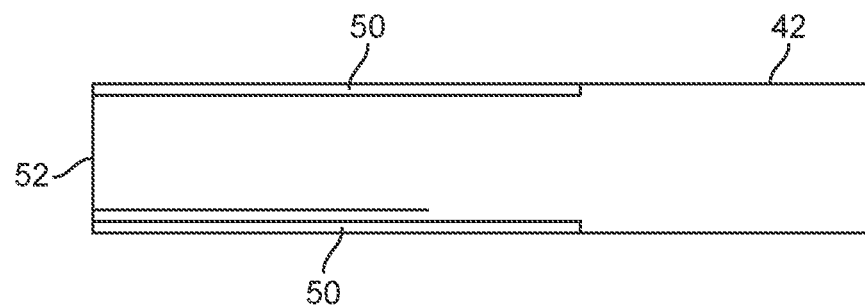
FIGS. 7A and 7B show side views of a hypotube which may be configured for attachment to a core wire.
Figure 7B:
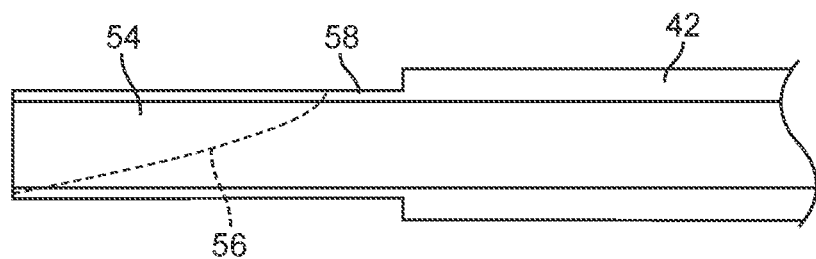
Figure 7C:
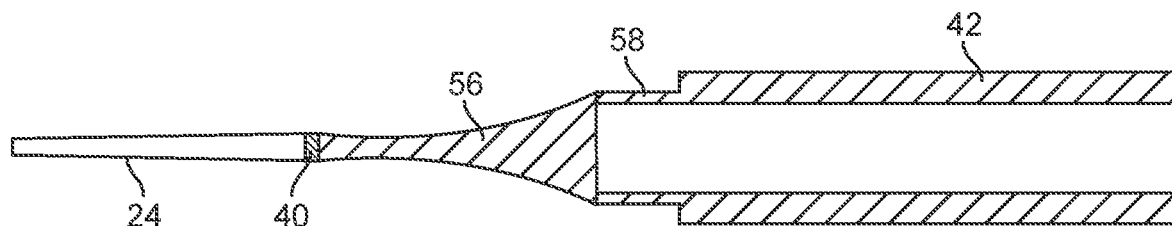
FIGS. 7C and 7D show top views of a hypotube attached to a core wire and integrally forming a guidewire having one or more electrodes integrated therealong.
Figure 7D:
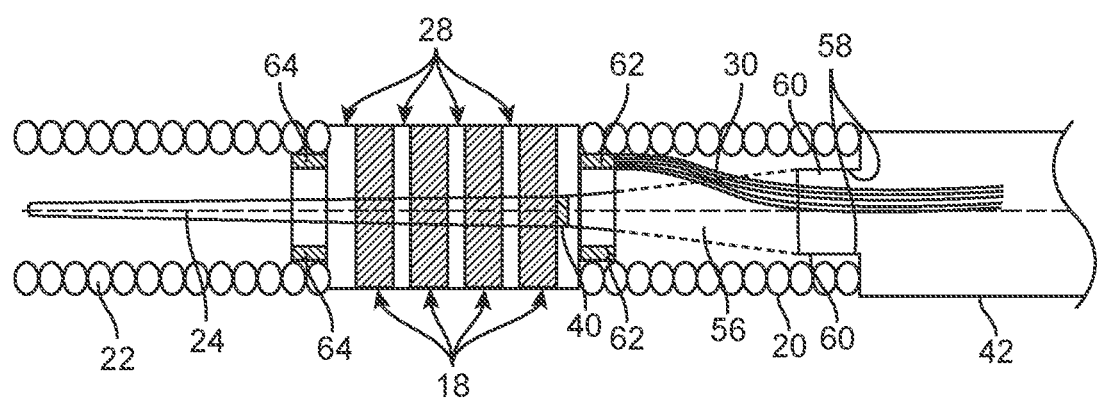

As seen in the top view of FIG. 7C, the resulting tapered distal section 56 may be narrowed down to a width of, e.g., 0.005 in., which may correspond to a diameter of the core wire 24. The narrowed end of the distal section 56 may be coupled directly to one another via attachment 40 (using any of the attachment methods herein) such that the core wire 24 and connected distal section 56 form a direct and integrated structure. With core wire 24 positioned within the distal coil 22, the electrode assembly may be connected to the proximal end of distal coil 22 via attachment 64 while proximal coil 20 may be connected to the proximal end of the electrode assembly via attachment 62 and to the shoulder 58 of hypotube 42 via attachment 60, as shown in the partial cross-sectional side view of FIG. 7D. The various attachments may be achieved through any number of attachment methods, e.g., solder joint, adhesively joined, etc.

While the attachment 40 between the core wire 24 and the tapered distal section 56 may be achieved via any of the attachment methods described above, the attachment may also alternatively use a clip or collar 70 (e.g., platinum tube, etc.) which may be placed over or upon the respective terminal ends. The terminal end of the core wire 24 may alternatively define a reduced section 66 (e.g., having a diameter of 0.012 in.) while the terminal end of the distal section 56 may similarly define a reduced section 68 (also having a similarly reduced diameter of 0.012 in.). The clip or collar 70 may be placed over each of the reduced sections 66, 68 and crimped or attached accordingly, e.g., laser or spot welded to respective reduced sections 66, 68, as shown in the detail side view of FIG. 7E.

Figure 8A:
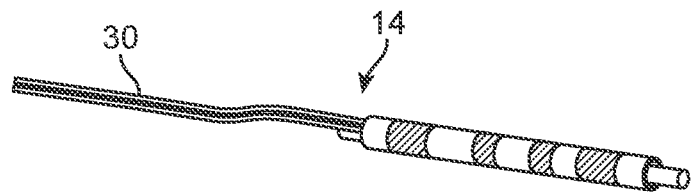
FIGS. 8A to 8D show perspective views of another variation for assembling a guidewire having one or more electrodes positioned therealong.
Figure 8B:
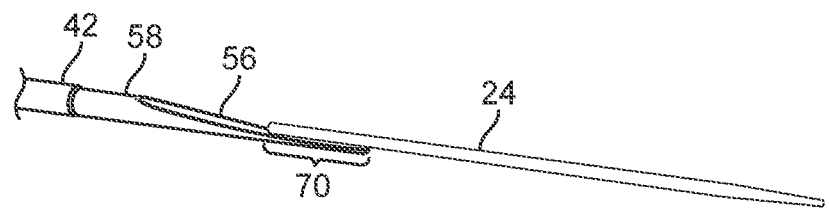
Figure 8C:
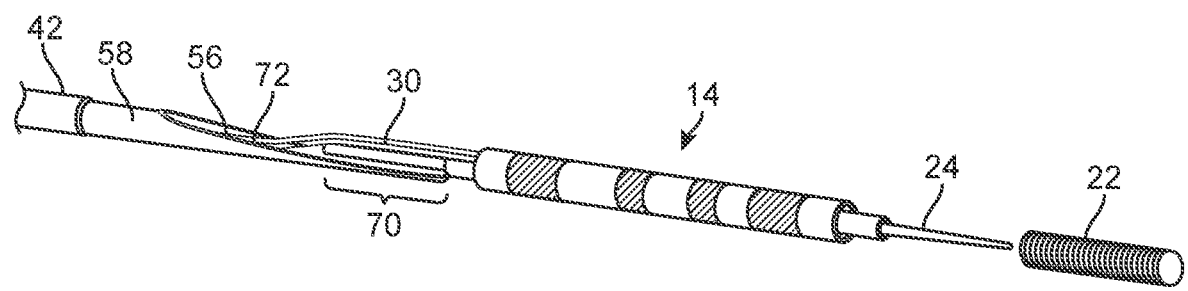
Figure 8D:
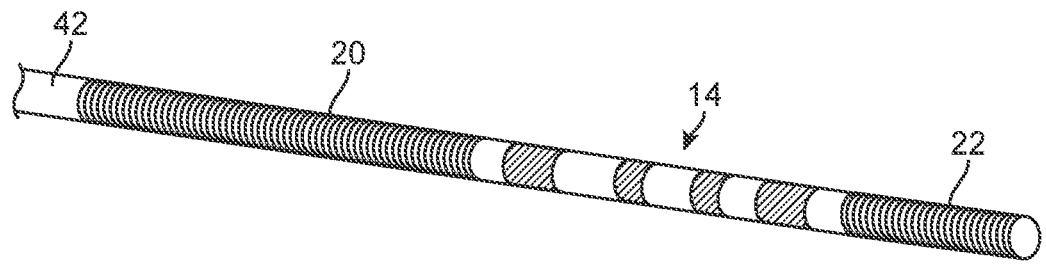

In yet another variation for manufacturing the guidewire assembly, FIGS. 8A to 8D show perspective views illustrating another example of how an electrode assembly 14 having one or more corresponding conductive wires 30, as shown in FIG. 8A, may be assembled with a core wire 24 joined directly to a tapered portion 56 of the hypotube 42, as shown in FIG. 8B. A proximal section of the core wire 24 may be joined along an attachment region 70 to a distal section 56 of the tapered hypotube 42. The core wire 24 may be attached utilizing any number of attachment methods described herein. With the core wire 24 and hypotube 42 coupled, the electrode assembly 14 may be placed along the core wire 24 and the wires 30 passed through the hypotube lumen 72, as shown in FIG. 8C. The proximal and distal coils 20, 22 may also be attached proximally and distally of the electrode assembly 14, as shown in FIG. 8D and as described herein.

Figure 9:
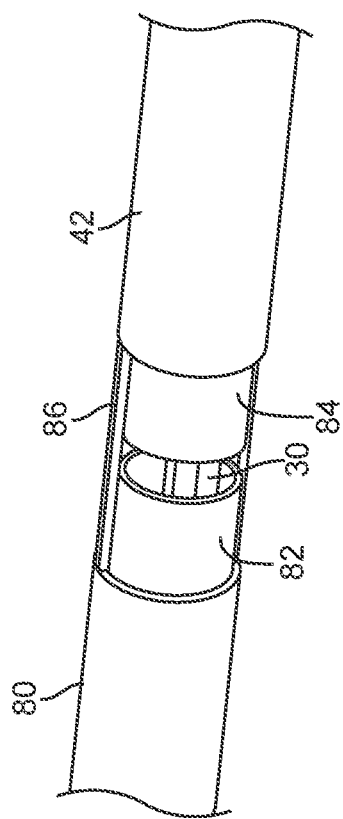
FIG. 9 shows a detail perspective view for coupling a hypotube to a second tubular member for forming a guidewire.

Additionally and/or optionally, in the event that a second hypotube 80 is joined to the hypotube 42, a reduced section 82 of second hypotube 80 and a reduced section 84 of hypotube 42 may be coupled to one another via a clip or collar 86, e.g., platinum tube, which may be laser or spot welded to the respective reduced sections 82, 84, as shown in the detail perspective view of FIG. 9.

Figure 10:
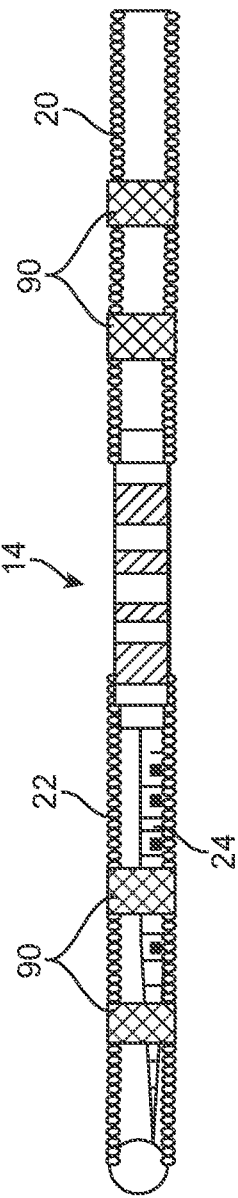
FIG. 10 shows a partial cross-sectional side view of one method for placing one or more radio-opaque bands on the guidewire.

In the event that any of the guidewire assemblies described herein require one or more radio-opaque markers to be integrated along its length, any number of crimping or attachment methods may be utilized. One additional and/or optional variation is shown in the partial cross-sectional side view of FIG. 10 which shows a guidewire assembly having one or more radio-opaque markers 90 attached. Such markers 90 may be attached, e.g., by gold solder formed upon the respective coiled sections. By omitting any metal components for the markers 90, the number of steps may be reduced in manufacturing the guidewire and may further avoid any increase in guidewire profile.

Figure 11:
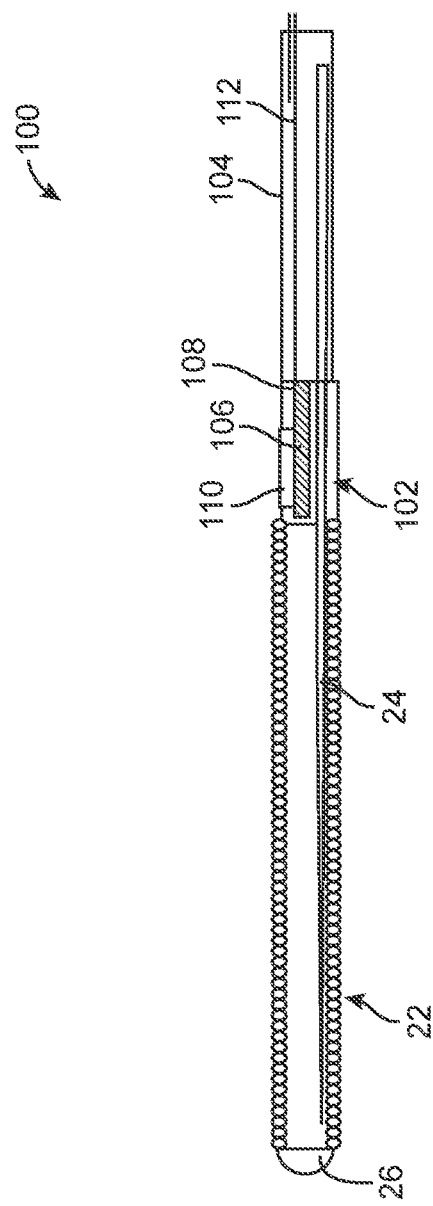
FIG. 11 shows a partial cross-sectional side view of a guidewire incorporating a continuous core wire through a pressure sensor housing.

Aside from the integration of an electrode assembly along the guidewire, the guidewire assembly may also optionally incorporate one or more sensors along its length. Although any number of sensors for detecting physiological parameters may be integrated, one particular sensor may include a pressure sensor for detecting intravascular fluid pressure. A partial cross-sectional side view is shown in FIG. 11 to illustrate an example of the relative positioning of the pressure sensor within or along the guidewire. As shown, the pressure sensing guidewire assembly 100 may have the pressure sensor housing 102 secured along the guidewire body at or near the terminal end 26 of the guidewire such that the diaphragm 106 of substrate 108 is exposed through slot 110 for contact with the surrounding fluid. The guidewire assembly 100 may further include the core wire 24 passing through the guidewire and sensor housing 102. The distal coiled body 22 of the guidewire assembly 100 may extend distally from the sensor housing 102 while the leads 112 connecting the diaphragm 106 and substrate 108 may pass proximally through the guidewire body 104 that is encapsulated in one or more polymers along its length may also be seen for connection to another module, e.g., a processor, monitor, etc., located outside the patient's body in use.

Figure 12A:
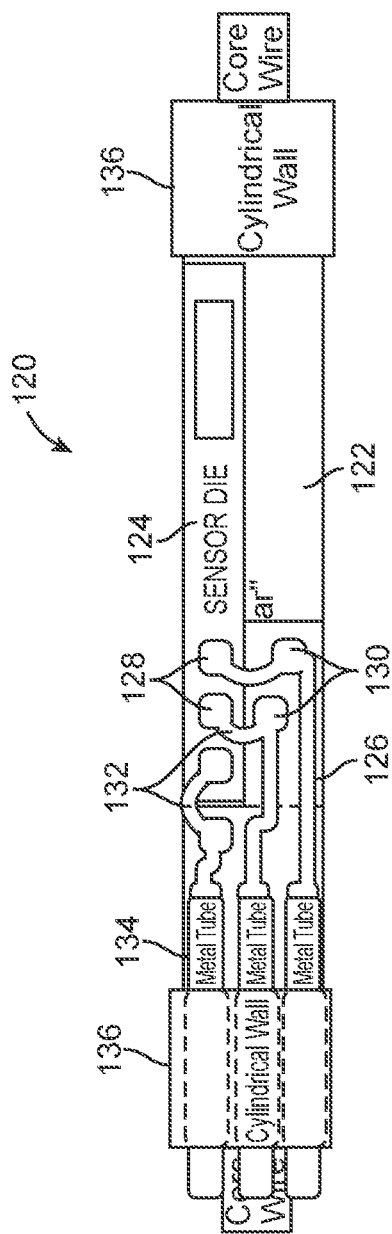
FIGS. 12A and 12B show top and side views of a pressure sensor die positioned directly upon a floor of the sensor housing.
Figure 12B:
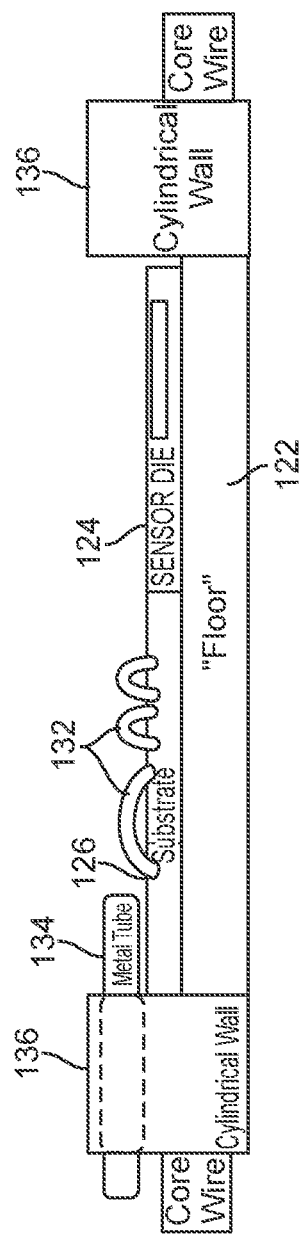

Because of the sensitive nature of the sensor, the pressure sensor diaphragm may be generally insulated from stress, e.g., by omitting coatings or epoxy from areas beneath and/or over the diaphragms. Hence, the regions around the wirebonding connecting the sensor to a substrate or conducting wires are ideal areas for maintaining low stress regions. One example for assembling a pressure sensor having low stress attachment may be seen in the top and side views of FIGS. 12A and 12B which show pressure sensor assembly 120 which may be integrated along the guidewire assembly. As shown in FIG. 12A, a platform 122 either formed directly along the core wire or along a separate platform integrated along the core wire or guidewire body may be used as a floor for attaching the various components of a pressure sensor. The platform 122 may be secured between apposed cylindrical walls 136 and the walls 136 and platform 122 may be secured to the core wire or a distal and proximal portion of a core wire may be attached at respective distal and proximal locations along the cylindrical walls 136.

As shown, the pressure sensor die 124 and substrate 126 (e.g., PCB substrate, flex circuit, etc.) may be attached directly to the floor 122 between the walls 136. One or more conductive wires 134 may be secured through the proximal cylindrical wall 136 such that the exposed terminal ends of the wires 134 may be electrically attached to the substrate 126. Electrical connections between the pressure sensor die 124 and substrate 126 may be made by wirebonds 132 coupling respective conductive pads 128, 130 which are also electrically coupled to the one or more conductive wires 134. The wirebonds 132 may have a loop height generally about, e.g., 0.001 to 0.002 in., above the surface of the substrate 126 with a wirebond outer diameter of about, e.g., 0.001 in., as shown in the side view of FIG. 12B. With this configuration of the pressure sensor die 124 and substrate 126 placed directly upon the floor 122, the assembly may maintain a low profile for integration along the guidewire body. Aside from utilizing wirebonds, flip chip methods of bonding using stud bumps can also be utilized to save space (as described in further detail herein).

In mounting or attaching the conductive wires along the sensor assembly, such as the substrate 126 or pressure sensor die 124, various methods may be used for electrically and mechanically bonding the wires along the sensor assembly to maintain a low profile configuration for integrating along the guidewire assembly. One example may be to form a surface mount configuration where an assembly jig 140 such as the one shown in the top view of FIG. 13A may be used. The assembly jig 140 may define a surface having a recess 142 which is sized to receive the substrate or die to be mounted in a secure fitting. One or more channels 144 may be defined along the jig 140 extending from one or more openings 146A, 146B, 146C directly to the recess 142. The number of channels 144 may correspond to the number of conductive wires 148 to be surface mounted along the substrate or die. Moreover, the channels 144 may be angled and/or tapered to facilitate guidance of the wires 148 directly to the recess 142.

Figure 13A:
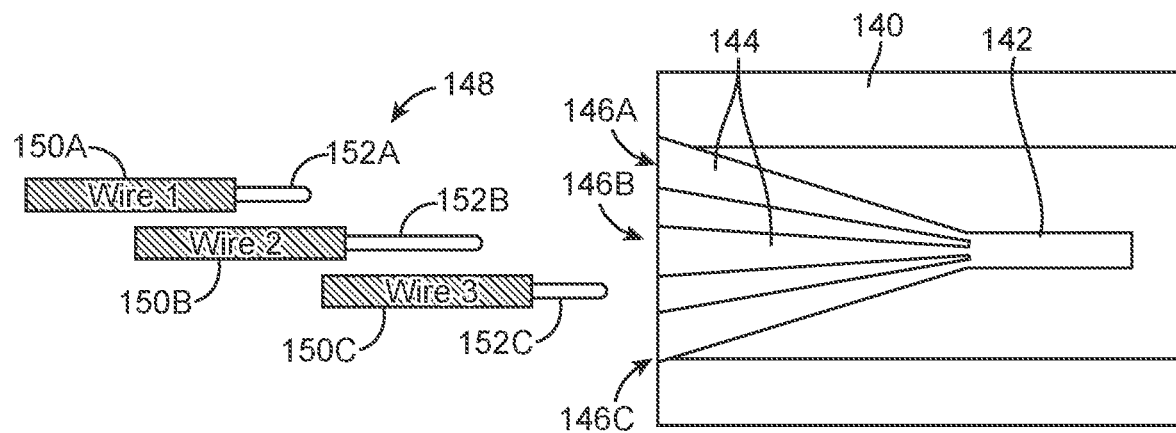
FIGS. 13A and 13B illustrate a top view of an assembly jig which may be used to attach one or more conductive wires to a pressure sensor die.
Figure 13B:
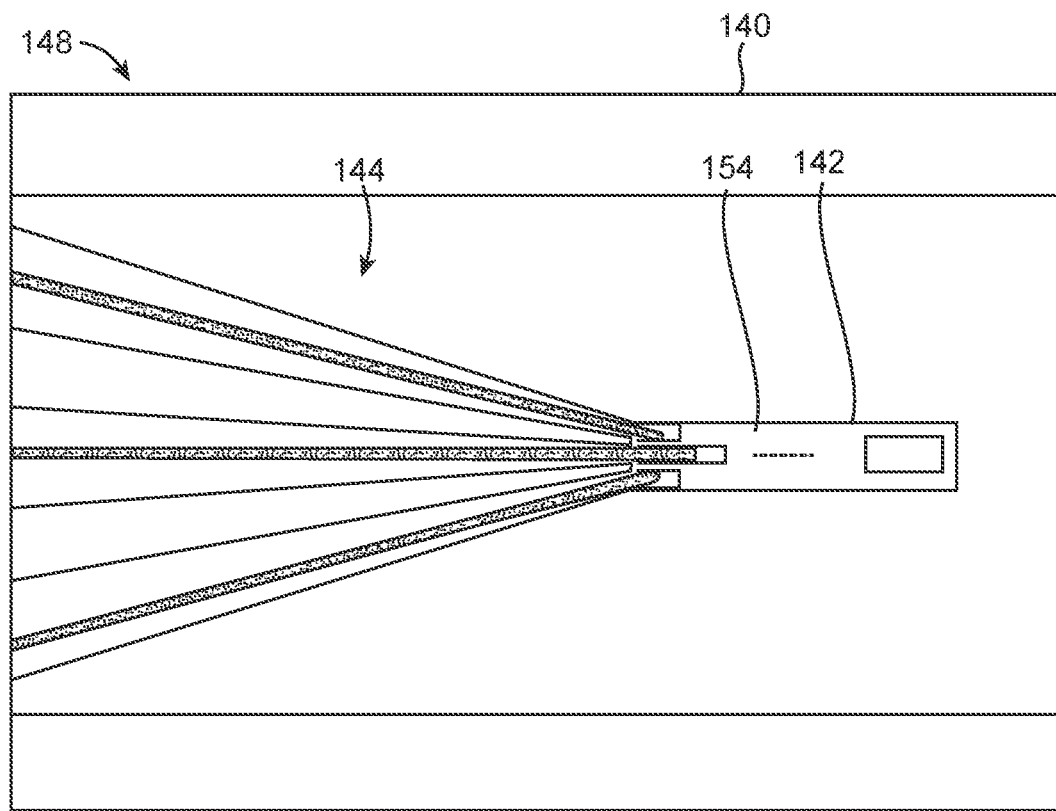

The conductive wires 150A, 150B, 150C, shown in this example as three wires although fewer or greater number of wires may be used, may each have their terminal ends 152A, 152B, 152C exposed for attachment, as shown in FIG. 13A. The wires 150A, 150B, 150C may be inserted through a respective opening 146A, 146B, 146C and placed into proximity to, e.g., a pressure sensor die 154, positioned within the recess 142, where the exposed terminal ends 152A, 152B, 152C may then be soldered or otherwise attached directly to the pressure sensor die 154, in this example although other substrates may also be used, and as shown in FIG. 13B.

Figure 14A:
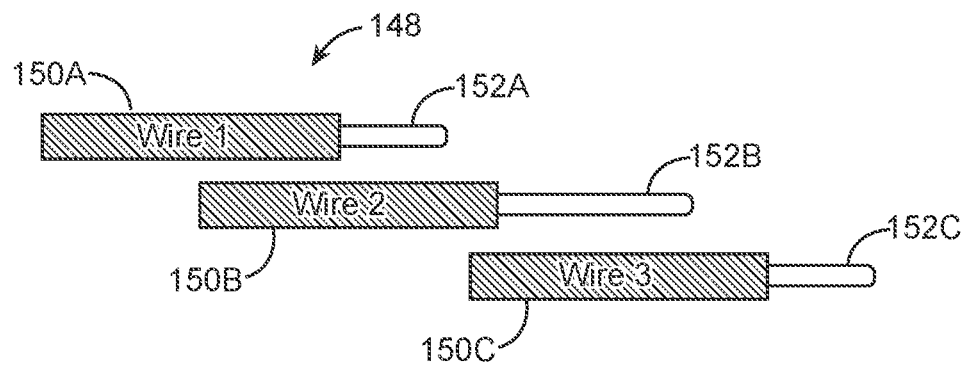
FIGS. 14A and 14B show side and end views of one or more conductive wires and an end cap which may be used to position and maintain the wires relative to a pressure sensor die.
Figure 14B:
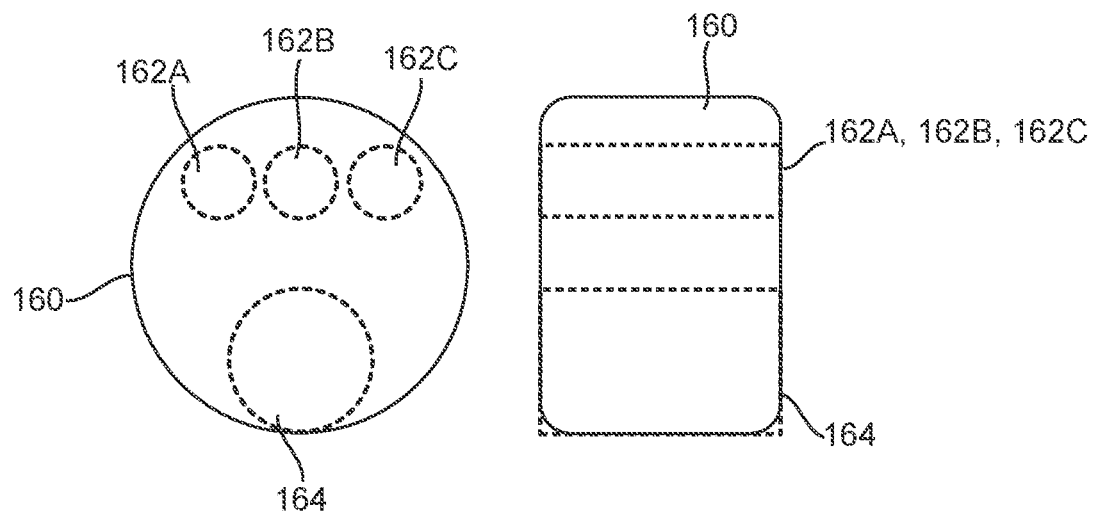

Additionally and/or alternatively, rather than directly attaching the wires 148 to the die surface, an optional endcap 160 fabricated from a metal or plastic may be used to alleviate any stresses which may be imparted between the attachment of wires 148 to the sensor die 154. An example is shown in the end and side views of FIGS. 14A and 14B which illustrate a cylindrical endcap 160 (also shown as the cylindrical wall 136 in FIGS. 12A and 12B). The endcap 160 may have a diameter consistent with the diameter of the guidewire and may further define one or more wire receiving openings 162A, 162B, 162C each having a diameter of, e.g., 0.0015 to 0.003 in, for receiving a corresponding wire. Fewer than three or more than three openings may be utilized depending upon the number of wires used. Alternatively, the openings may be sized to accommodate two or more wires and the openings may be sized in different configurations depending upon the number of wires passed through the openings. An additional core wire opening 164 having a diameter of, e.g., 0.003 to 0.006 in., may also be defined through the endcap 160. The position of the core wire opening 164 can either be concentric or off-centered depending on space availability and performance requirements.

Figure 15A:
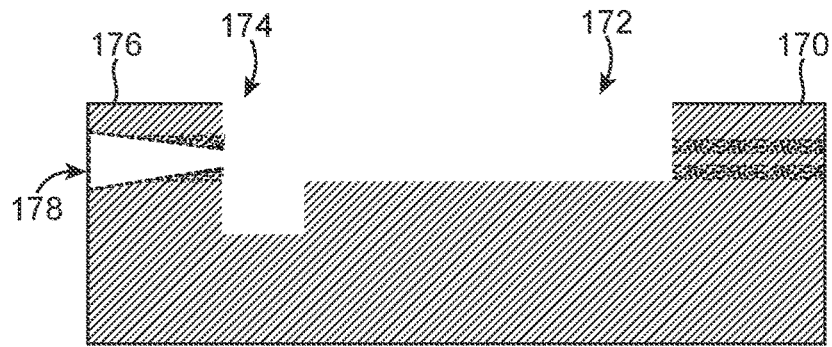
FIGS. 15A to 15D illustrate partial cross-sectional side views of another variation for attaching one or more wires through an endcap and onto a pressure sensor die.
Figure 15B:
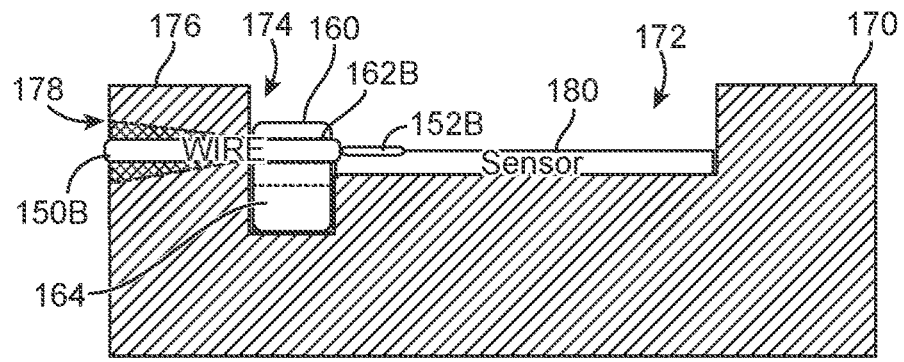

FIGS. 15A to 15D show partial cross-sectional side views of another variation for surface mounting or attaching conductive wires to a substrate or pressure sensor die using the endcap 160. As shown in FIG. 15A, the assembly jig 170 may similarly define a recess 172 sized to receive a substrate or sensor die upon which the wires are to be connected. The jig 170 may further define an endcap channel or recess 174 at a location adjacent to where the wire channels 178 are defined through a wire guide 176. The endcap channel or recess 174 may extend into the jig 170 at a depth sufficient to accommodate the diameter of the endcap 160 such that the openings 162B through the endcap 160 align with the wire channels 178 and substrate or die when positioned within the recess 172, as shown in the partial cross-sectional side view of FIG. 15B.

Figure 15C:
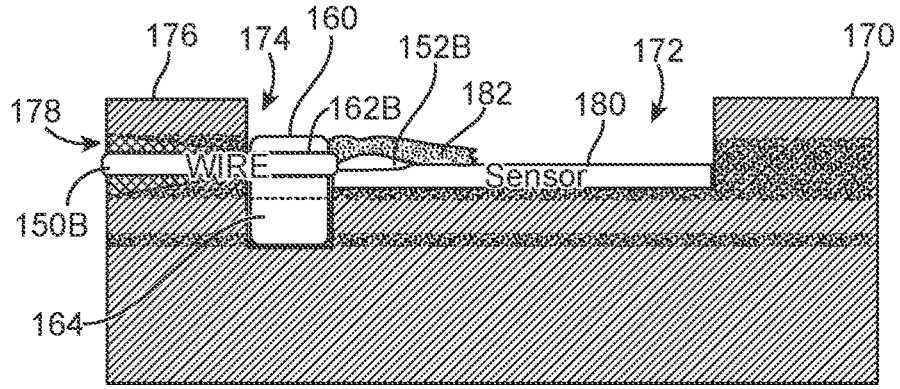
Figure 15D:
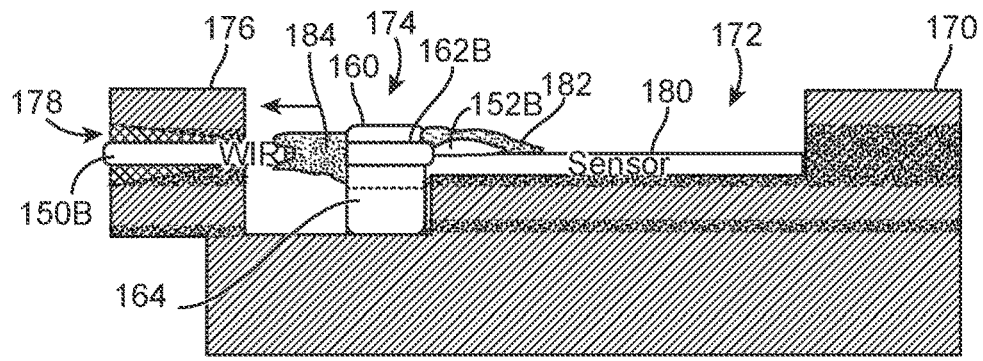

With the one or more wires 150B inserted through the corresponding wire channel 178 and endcap opening 162B, the exposed terminal end 152B may be placed upon the conductive pad along the pressure sensor die 180 positioned adjacent to the endcap 160 and within the recess 172. The terminal end 152B may then be attached or appropriately surface-mounted upon the sensor 180 through any number of attachment methods such as solder, conductive epoxy, etc. optionally followed by an additional overcoat 182, as shown in FIG. 15C. The wire guide 176 may be slidably attached to the remainder of the jig 170 such that the guide 176 may be retracted to expose the endcap 160. The junction formed between the entry location of the wire 150B and endcap 160 may also be attached relative to one another using any number of attachment methods described above. The attachment may be followed by an optional overcoat 184, as shown in FIG. 15D. Once the attachment has been completed, the sensor 180, endcap 160, and wire 152B assembly may be removed from the jig 170 for assembly into the guidewire.

Figure 16A:
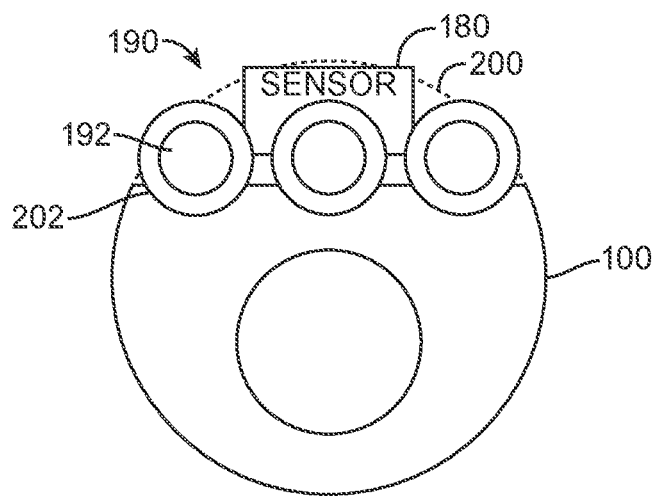
FIGS. 16A to 16C show respective end, side, and top views of a flip-chip assembly method for attaching a pressure sensor die directly to a sensor housing.
Figure 16B:
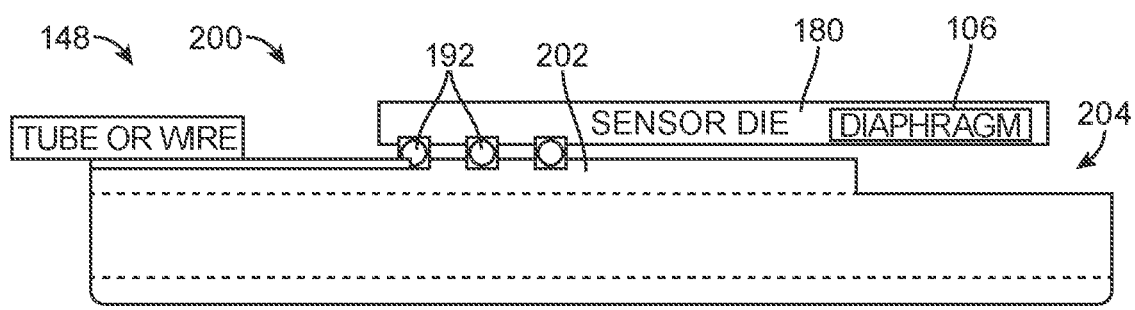
Figure 16C:
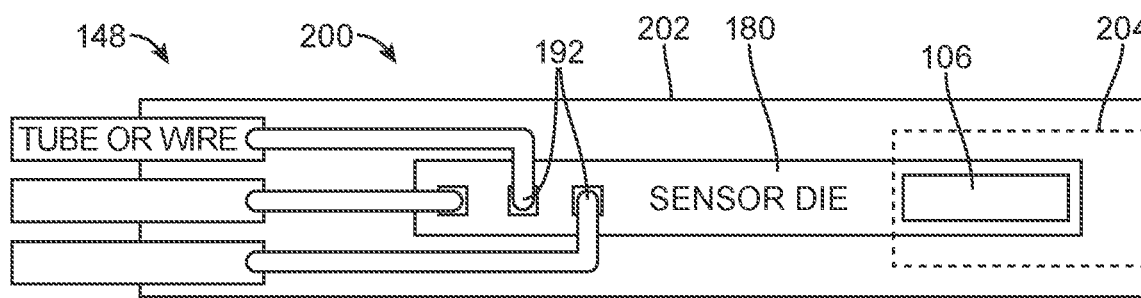

In yet another example for integrating a pressure sensor assembly 190 into a guidewire while maintaining a low profile configuration, FIGS. 16A to 16C show another variation in the end, side, and top views where the pressure sensor die 180 may be electrically connected directly to one or more conductive wires 148 through attachment via conductive pads 192 utilizing a flip chip type mounting configuration. In the arrangement shown, the one or more conductive wires 148 may be routed through the guidewire and into proximity to the pressure sensor mounting region 200 defined along the guidewire. Within the mounting region 200, a platform or floor 202 formed along the region 200 may be further form recessed region 204 which may be formed as a recess within the platform 202. With the pressure sensor die 180 inverted relative to the platform 202, the conductive wires 148 may be electrically connected directly to the respective conductive pads 192 located along the surface of the pressure sensor die 180. Moreover, by inverting the pressure sensor die 180 the location of the diaphragm 106 may also be inverted to become placed in apposition to the platform 202, as shown in the side view of FIG. 16B, directly over the recessed region 204, as further shown in the top view of FIG. 16C. Hence, the diaphragm 106 may remain exposed over the region 204 and uninhibited so as to allow for the sensing of physiological parameters such as fluid pressure. It is also possible to make the diaphragm 106 and the conductive pads on the sensor die 192 on the opposite surfaces of the pressure sensor by a technique referred to as Through Silicone Via (TSV). In such a case, the same technique of using the flip chip method described above can be utilized with or without having any recess in the platform 202.

Figure 17A:
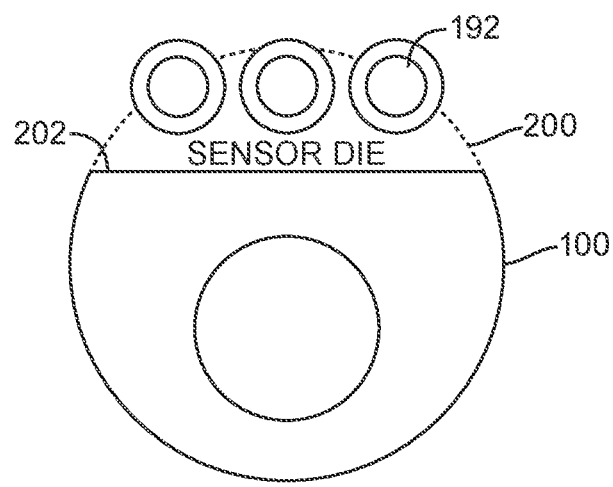
FIGS. 17A to 17C show respective end, side, and top views of another method for attaching the pressure sensor die directly to the sensor housing.
Figure 17B:
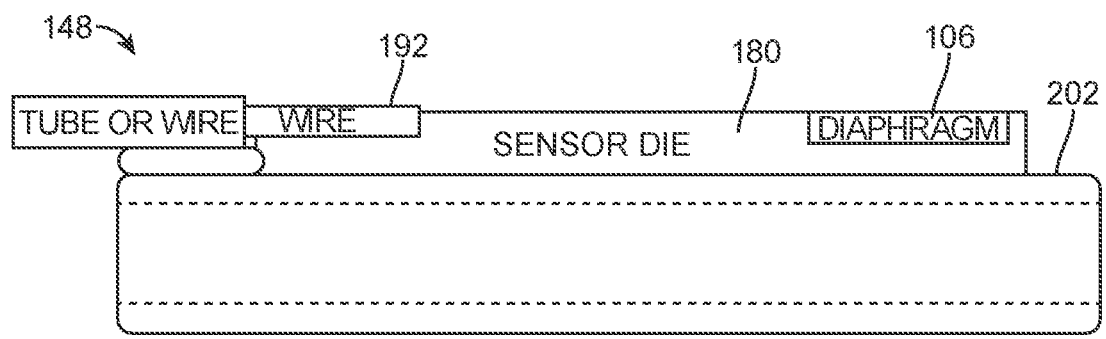
Figure 17C:
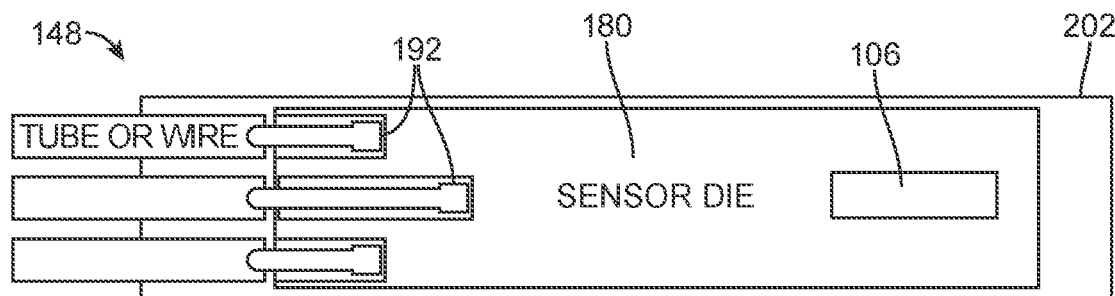

Another example for mounting the pressure sensor die 180 along the guidewire in a low profile is further shown in the end, side, and top views of FIGS. 17A to 17C. In this variation, the pressure sensor die 180 may be mounted directly to the platform or floor 202 thus allowing for the direct surface mounting of the once or more wires 148 to the respective conductive pads 192 along the surface of the sensor die 180. This variation also allows for the direct exposure of the diaphragm 106 for sensing physiological parameters. Additionally, this variation may also present the shortest overall height of the pressure sensor relative to the platform 202 thus allowing for a low profile and may also accommodate a relatively wider die.

Figure 18:
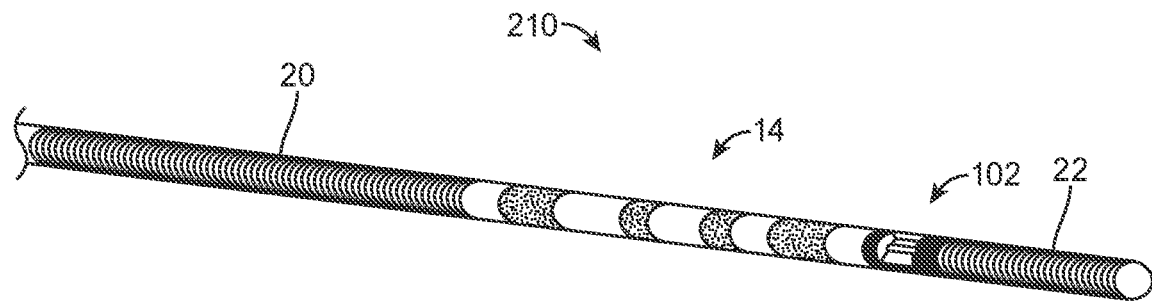
FIG. 18 shows a perspective view of a guidewire having the one or more electrodes and a pressure sensor integrated directly into the guidewire.

FIG. 18 illustrates a perspective view of an electrode and pressure sensing assembly integrated along a single guidewire 210. Although the electrode assembly 14 is shown proximal to the pressure sensing housing 102 along the guidewire body, the pressure sensing housing 102 may alternatively be located proximal to the electrode assembly 14 instead. To electrically couple each of the electrodes and the pressure sensor, multiple conductive wires may be routed through the length of the guidewire but to ensure that the multiple wires are ordered and remain untangled, the wires may be bundled relative to one another.

Figure 19A:
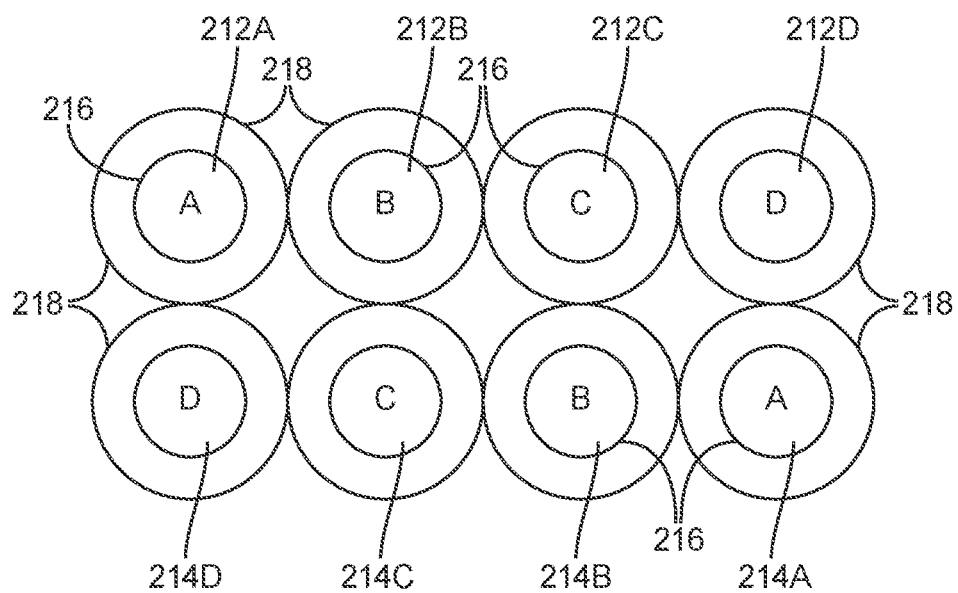
FIG. 19A shows a cross-sectional end view of one variation for aligning multiple conductive wires through the guidewire.
Figure 19B:
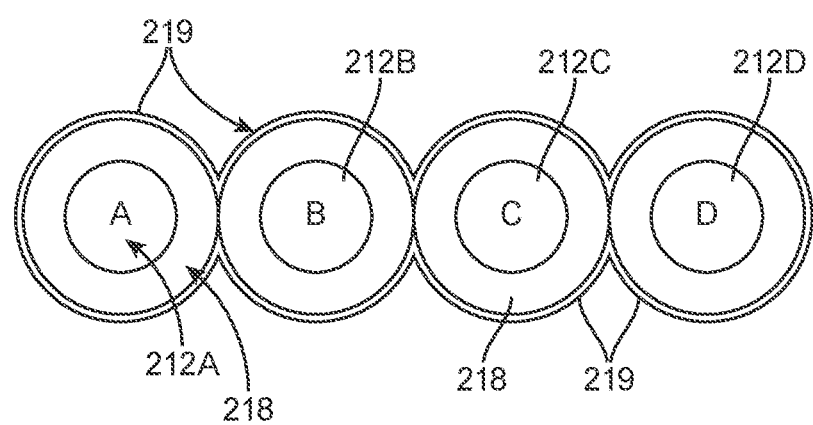
FIG. 19B shows a cross-sectional end view of another variation of aligned multiple conductive wires having an optional metallization layer coated over the assembly.

FIG. 19A shows a cross-sectional end view illustrating how multiple conductive wires 212A, 212B, 212C, 212D and conductive wires 214A, 214B, 214C, 214D may be positioned relative to one another. While shown in this example with eight wires, this is intended to be illustrative and fewer than eight or greater than eight wires may be utilized in practice. Nonetheless, each of the wires may have a base coating 216, e.g., polyimide, and a further polymer matrix 218, e.g., pellathane matrix, surrounding each of the wires and forming an attachment to adjacent wires such that the wires form an ordered and stacked ribbon. Another variation to the conductor configuration may include an additional layer of metallization 219 over the coated polymer matrix 218, as shown in the end view of FIG. 19B. Such a metallization layer 219 may have a thickness of, e.g., 2 to 5 microns, and can be added by processes well known in the art such as chemical vapor deposition where metals such as copper, gold, aluminum, etc., are commonly deposited on a substrate (such as polyimide or other polymers). In this case, the metallization layer 219 may be deposited over the polymer matrix 218. The metallization layer 219 can serve several functions such as electrically isolating the conducting wires from Electro Magnetic (EM) Coupling thus providing an EM shield. This may be desirable in many sensor applications where external noise coupling needs to be avoided.

Figure 20A:
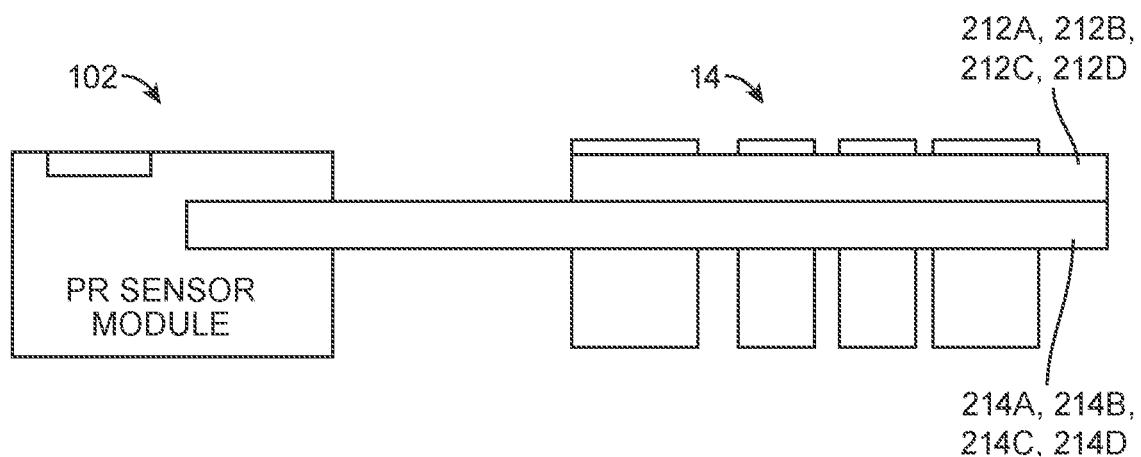
FIG. 20A shows one variation for terminating a first set of conductive wires at the one or more electrodes and a second set of conductive wires at the pressure sensor assembly.

With the conductive wires accordingly stacked and aligned, a first row of wires, e.g., wires 212A, 212B, 212C, 212D, may be assigned for electrical coupling to the corresponding number of electrodes while the second row of wires, e.g., wires 214A, 214B, 214C, 214D, may be assigned for electrical coupling to the pressure sensor assembly 102. FIG. 20A shows an example of how the first row of wires may terminate at the electrode assembly 14 through the guidewire while the second row of wires may continue on through the guidewire for coupling to the pressure sensor assembly 102.

Figure 20B:
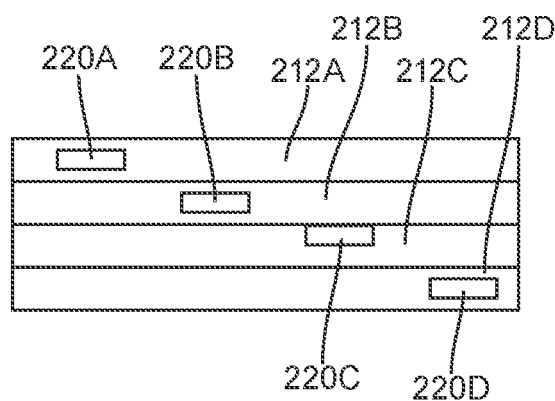
FIG. 20B shows a top view of conductive wires which may have offset exposed portions for electrical coupling.
Figure 20C:
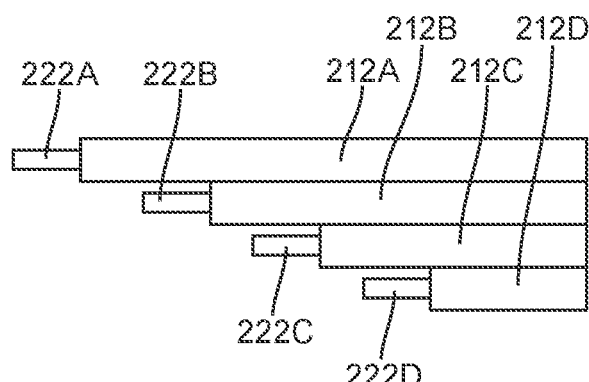
FIG. 20C shows a top view of conductive wires illustrating how the terminal ends may be offset for electrical coupling.

Another example is illustrated in the top view of FIG. 20B which shows how portions of the conductive wires may be processed to have exposed selective regions 220A, 220B, 220C, 220D through the insulative covering at uniform or staggered longitudinal locations for electrically coupling to electrodes or sensors. Alternatively, the terminal ends of the wires may be cut such that the exposed terminal portions 222A, 222B, 222C, 222D are positioned at staggered lengths relative to one another, as shown in the top view of FIG. 20C.

Figure 21:
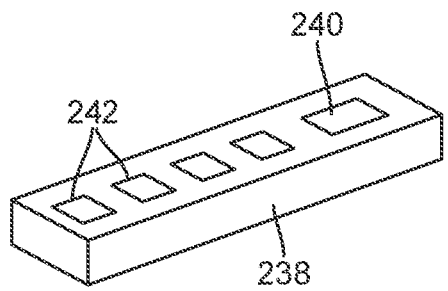
FIG. 21 show a perspective view of a pressure sensor die to be secured to an electrode assembly along a guidewire.
Figure 22B:
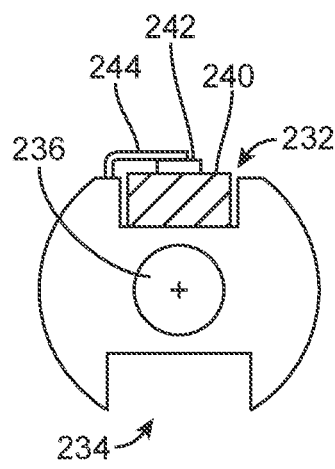
FIGS. 22A and 22B show perspective and end views of another variation of a guidewire having a defined channel for positioning of the pressure sensor.
Figure 22A:
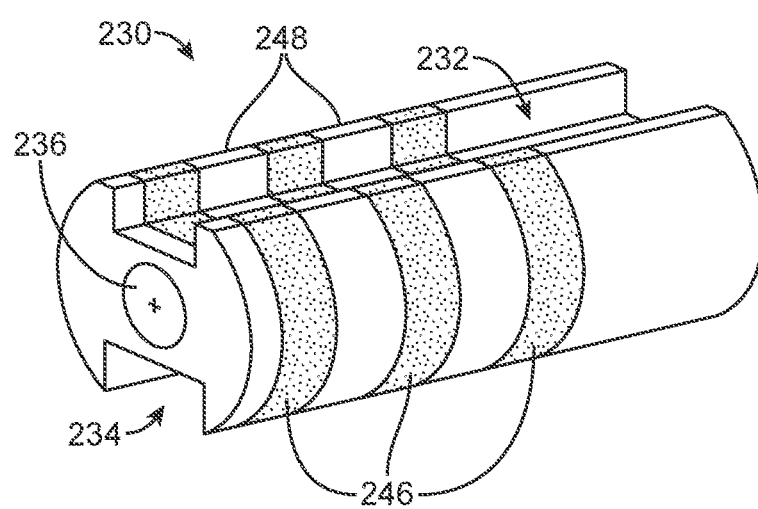

In yet another variation for mounting a pressure sensor die 238 having a diaphragm 240 and one or more conductive pads 242, as shown in the perspective view of FIG. 21, FIG. 22A shows a perspective view of an electrode assembly 230 which may be formed as a composite assembly to which the sensor die 238 may be mounted directly upon. The electrode assembly 230 may be formed to have one or more electrode segments 246 (e.g., fabricated from a conductive material such as gold or other metallic) alternated with one or more corresponding insulating segments 248 (e.g., fabricated from polyimide or other polymeric material or another electrically insulative material). Each of the electrode segments 246 may be patterned and removed (e.g., EDM, laser cut, etc.) from a sheet or layer of conductive material such that the electrode segments 246 are individually formed from the sheet or layer or stacked upon one another to form the composite structure.

The electrode assembly 230 may define a core wire receiving channel 236 through the length of the assembly and the outer surfaces of the assembly may define a sensor receiving slot 232 along a length of the assembly as well as an optional slot 234, e.g., for wiring, etc., along the length of the assembly opposite to the sensor receiving slot 232. The pressure sensor die 238 may be placed directly within the receiving slot 232 and electrically coupled via respective wirebonds 244 to conductive wires which may be passed through slot 234, as shown in the partial cross-sectional end view of FIG. 22B. Once the sensor die 238 has been wirebonded, the assembly may be potted using an appropriate material to provide for further mechanical strength and structural stability. The potting may be restricted to the conductive pads while remaining free from the sensor diaphragm 240. While wirebonding is shown as the attachment method from the sensor conductive pads to the conducting elements 246, other methods such as flip chip as described above can be utilized to attach the sensor die directly on the base of the channel 232. In this case the sensor dies may be fabricated such that the conducting pads 242 and the diaphragm 240 are on opposite faces of the sensor die 238. This can be achieved by sensor die fabrication methods know in the art such as TSV. Using such a method may yield a desirable profile to package the sensor along a 0.014 in. guidewire.

Figure 23A:
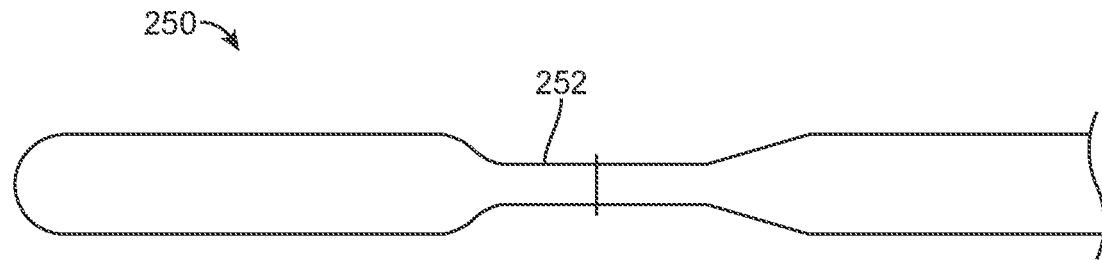
FIG. 23A shows a side view of a core wire having a reduced section for securing an electrode assembly.
Figure 23B:
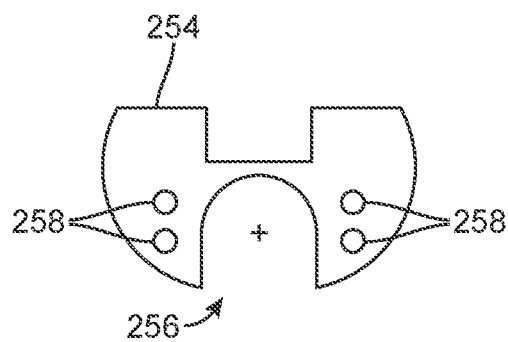
FIGS. 23B and 23C show end views of one variation of conductive and insulative segments for securement to the core wire.
Figure 23C:
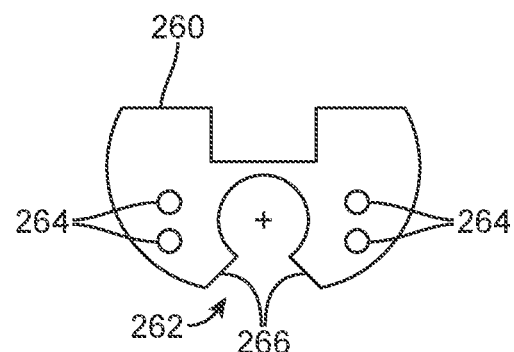

FIG. 23A illustrates a side view of a core wire 250 which may be configured to have a reduced section 252 along its length to provide a sensor mounting section. The reduced section 252 may have a cross-sectional area which is shaped into various configurations to facilitate the mounting or securement of the electrode assembly or other sensors along the section. One variation is illustrated in the end view of FIG. 23B which illustrates a conductive segment 254 and FIG. 23C which illustrates an insulating segment 260 which may be attached to the core wire 250 adjacent to the conductive segment 254. The conductive segment 254 may be formed to have one or more wire receiving channels 258 for passage of the conducting wires and the segment 254 may further define a core wire receiving channel 256 which may be optionally narrowed to provide for a snap fit over the reduced section 252. Similarly, the insulating segment 260 may also define one or more wire receiving channels 264 as well as a core wire receiving channel 262. The receiving channel 262 defined by the segment 260 may further define narrowed receiving members 266 which allow for the segment 260 to be snapped into place upon the reduced section 252. With the desired number of conductive segments 254 formed and the corresponding number of insulating segments 260 also formed, each of the segments 254, 260 may be secured upon the reduced section 252 in an alternating manner as well as secured to one another through various securement methods, e.g., adhesives, mechanical, etc.

Figure 23D:
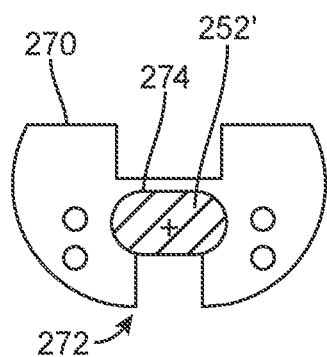
FIGS. 23D and 23E show end views of another variation of conductive segments which may be configured to the core wire having a predetermined cross-sectional shape.
Figure 23E:
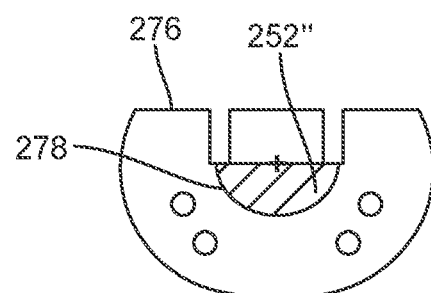

While the reduced section 252 may be formed to have a cross-sectional area which is shaped into various configurations, the receiving channels defined by the segments may be correspondingly configured as well. An example is shown in the end view of FIG. 23D which illustrates a conductive segment 270 defining a core wire receiving channel 272 which is formed into a receiving section 274 correspondingly shaped for placement upon a keyed core wire section 252', e.g., elliptical, rectangular, etc. Another variation is shown in the end view of FIG. 23E which also shows a conductive segment 276 having a configured receiving section 278 for securement to a correspondingly keyed core wire section 252", e.g., semi-spherical, etc. In this variation, the pressure sensor die may also be placed directly upon the reduced section 242". Other configurations of the reduced section 252 as well as the corresponding shapes defined by the segments may be utilized in other variations.

Figure 24:
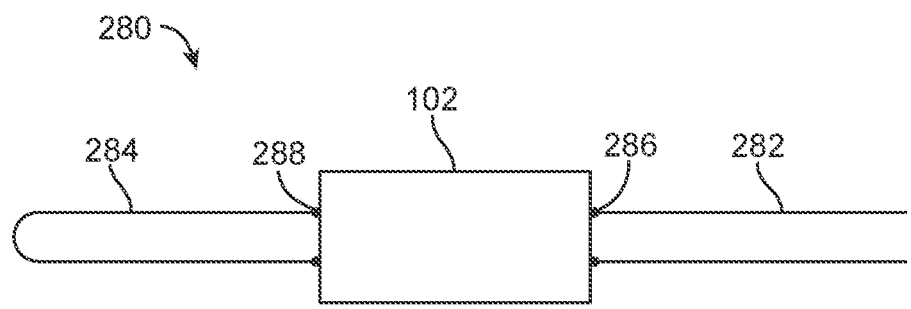
FIG. 24 shows a side view of another variation of a core wire which may be attached as separate portions to a pressure sensor housing.

In yet another variation, FIG. 24 shows a side view of an assembly having a discontinuous core wire 280 which may be separately attached to the sensor housing 102. A proximal core wire section 282 and a distal core wire section 284 may each be attached at their respective locations via any number of attachments 286, 288, e.g., welded joint, adhered attachment, etc. Such an arrangement may allow for maintaining adequate space for securement of the sensor along the housing 102 while maintaining a low profile guidewire assembly.

Figure 25A:
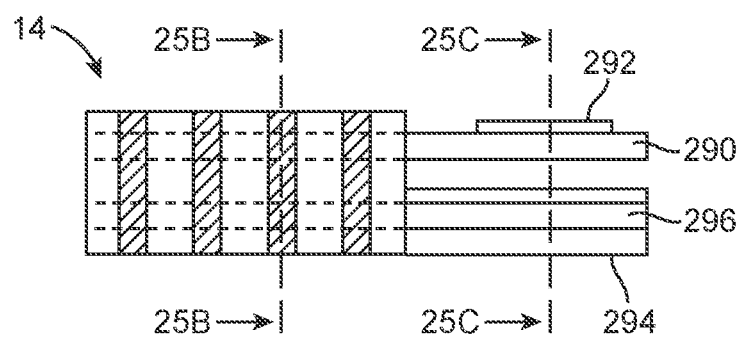
FIGS. 25A to 25C show side and end views of a pressure sensor die which may be cantilevered to reduce or eliminate any stresses imparted to the sensing diaphragm.
Figure 25B:
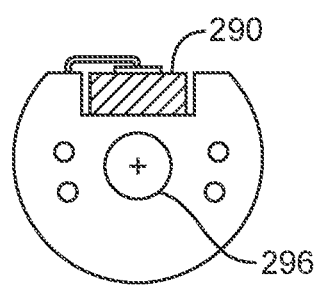
Figure 25C:
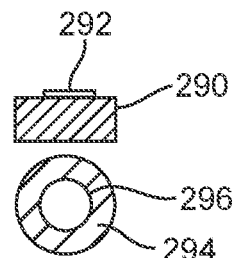

FIG. 25A shows a side view of yet another variation where the exposed diaphragm 292 of the pressure sensor die 290 may be isolated from any stresses which may be imparted by the guidewire or sensor die. The pressure sensor die 290 may be attached through the electrode assembly 14 such that the portion of the die 290 having the diaphragm 292 may extend proximally or distally from the electrode assembly 14 in a cantilevered manner remaining unattached beneath the die. A polymeric housing 294 defining a core wire receiving channel 296 may also extend through the electrode assembly 14 adjacent to the cantilevered sensor die 290, as shown in the end views of FIGS. 25B and 25C.

Figure 27A:
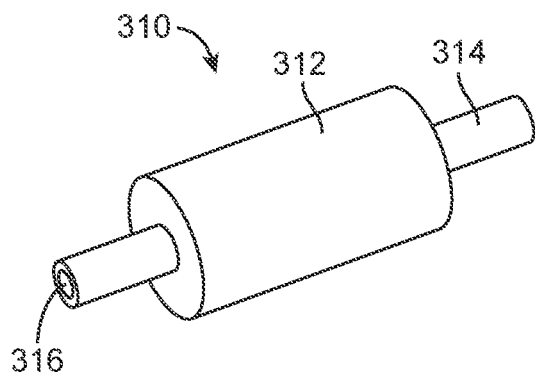
FIGS. 27A and 27B show perspective and end views of another variation of a core wire having a tubular pressure sensor housing secured around the core wire.
Figure 27B:
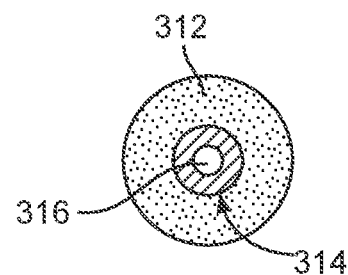

Another variation is shown in the side, end, and perspective views of FIGS. 26A to 26C which illustrates an electrode assembly 14 having an adjacently secured barrier segment 300, e.g., insulative disc, which defines a sensor opening 302 and core wire receiving channel 296. The sensor opening 302 may be configured as a passage, e.g., rectangular, which is sized to fit the pressure sensor through without necessarily contacting the pressure sensor so as to limit any transfer of stresses. The sensor opening 302 may also be scaled in size once the sensor has been placed to allow for its uninhibited passage Yet another variation is illustrated in the perspective and end views of FIGS. 27A and 27B which show an electrode assembly 310 which may be formed from a conductive tube 312 having a length of, e.g., 0.050 to 0.060 in., and a diameter of, e.g., 0.007 in., fabricated from a metallic material, e.g., stainless steel, platinum-iridium, etc. The conductive tube 312 may be attached or otherwise connected over an insulative tube 314, e.g., polyimide, etc., having a diameter of, e.g., 0.005 in., which may provide structural support to the electrode assembly 310 by holding and maintaining a position of each of the conductive segments as well as providing electrical insulation. The insulative tube 314 may define a core wire channel 316 through which the core wire may be positioned.

Figure 28A:
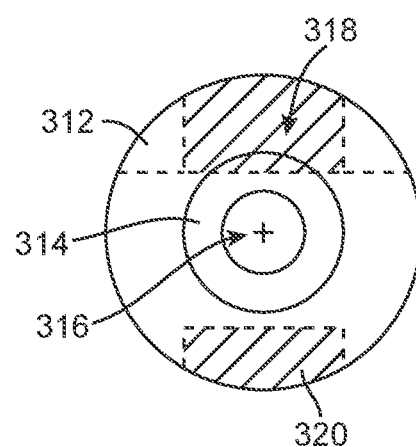
FIGS. 28A and 28B show end views illustrating an example of how material from the tubular pressure sensor housing may be removed for forming a pressure sensor receiving channel.
Figure 28B:
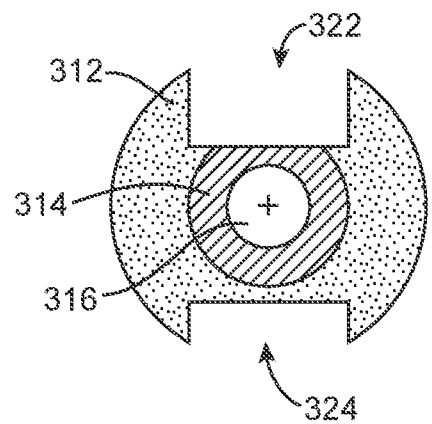

With the conductive tube 312, portions of the tubing may be removed to provide for space into which the pressure sensor die may be positioned. One example is shown in the end views of FIGS. 28A and 28B which illustrate how portions of the conductive tube 312 as well as portions of the insulative tube 314 may be removed as indicated by the removed section 318. The removed section 318 may have a width of, e.g., 0.007 in., and a height of, e.g., 0.0035 in., while an optionally removed section 320 may have a width of, e.g., in., as shown in FIG. 28A. The dimensions of the removed sections 318, 320 may be varied depending upon the size of the pressure sensor die used as well as the number of conducting wires. FIG. 28B illustrates the end view of the assembly having the sections 318, 320 removed to provide for a sensor channel 322 as well as an optional channel 324, e.g., for passage of wires.

Figure 29:
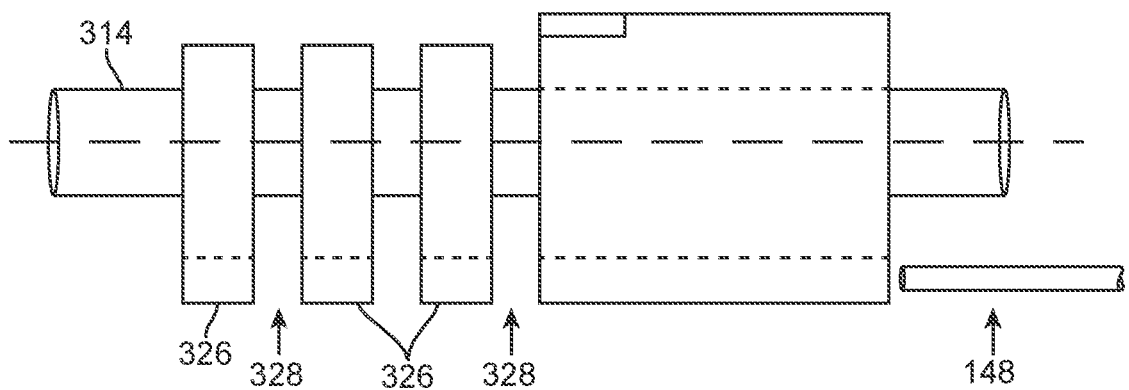
FIG. 29 shows a side view of the conductive segments and tubular pressure sensor housing secured upon the core wire.
Figure 30:
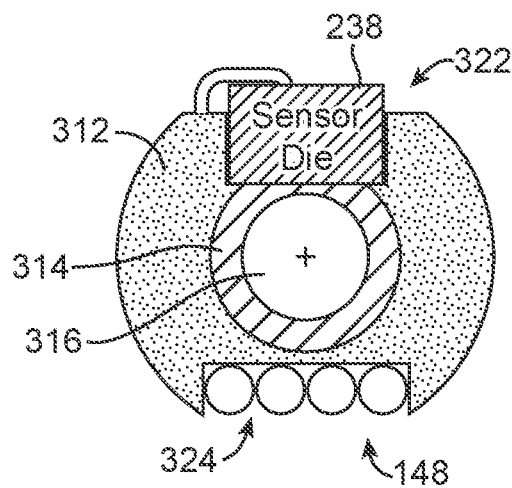
FIG. 30 shows an end view illustrating a pressure sensor die and conductive wires positioned upon the respective receiving slots.

With the respective channels formed, segments may be formed by the conductive tube 312 by removing selective portions of the material. An example is shown in the side view of FIG. 29 which illustrates portions of the conductive tube 312 removed to form conductive segments 326. The formed gaps 328 between each of the conductive segments 326 where material has been removed may have a width of, e.g., 0.001 to 0.002 in., to provide for the placement of electrically insulative materials within. FIG. 30 illustrates an end view of the conductive segments 326 having a pressure sensor die 238 positioned along the sensor channel 322 and one or more conductive wires 148 positioned along the optional channel 324. It should be noted that while a method of obtaining the metal pattern on a insulative material is described, other methods such as selectively metalizing a 3D polymer surface (such as a cylinder or a rectangle with required features such as a core wire hole) via vapor deposition and photo masking it is feasible to create similar patterns and achieve the desired function.

Guidewire Conducting Wires

Various methods of running signal conducting elements (wires, groups of wires, optic fiber in case of optical sensors) through a hypotube have been previously described. These methods involve extensive pre-preparation of the conducting elements and/or careful handling to construct the guidewire assembly. Yet another method for constructing a guidewire having a low profile is described which enables the construction of a guidewire with little compromise of its mechanical properties while at the same time enables the mounting of multiple sensors on the guidewire device.

Figure 31:
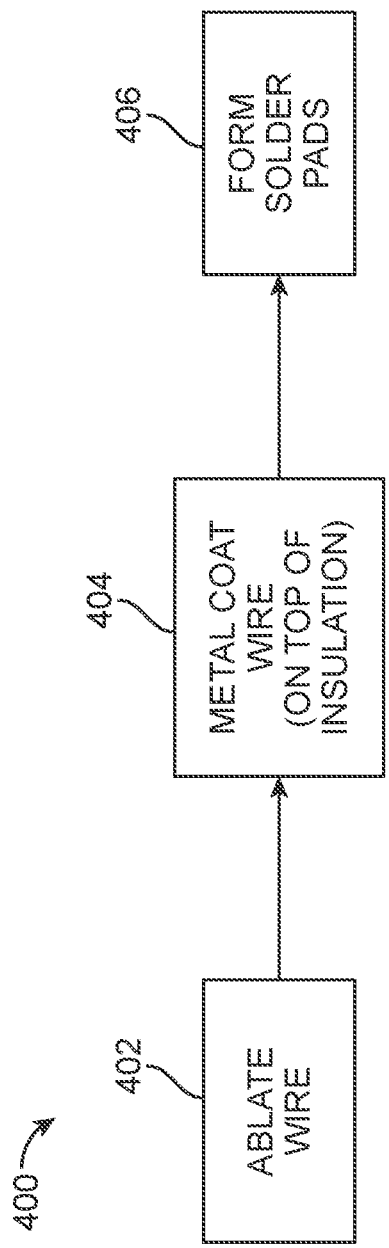
FIG. 31 shows a process flow diagram for one particular method for selectively forming isolated pads with respect to one or more conducting wires.
Figure 32:
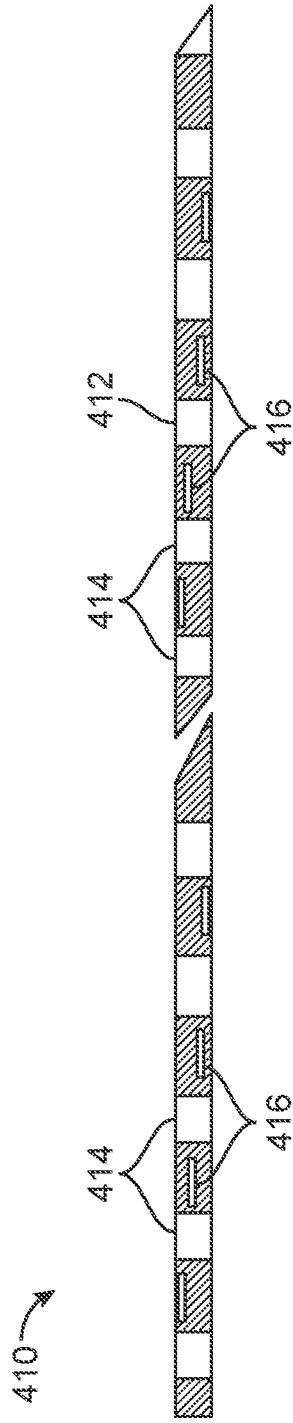
FIG. 32 shows a wire assembly in which selective regions of the wire have been ablated through the surrounding insulation and to the underlying individual selected conducting wire.
Figure 35A:
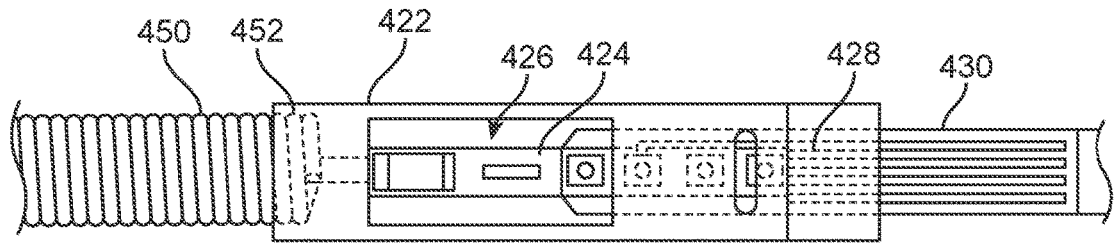
FIGS. 35A to 35D show respective top, side, transparent perspective, and perspective views of another variation of the sensor casing and its components.
Figure 35B:
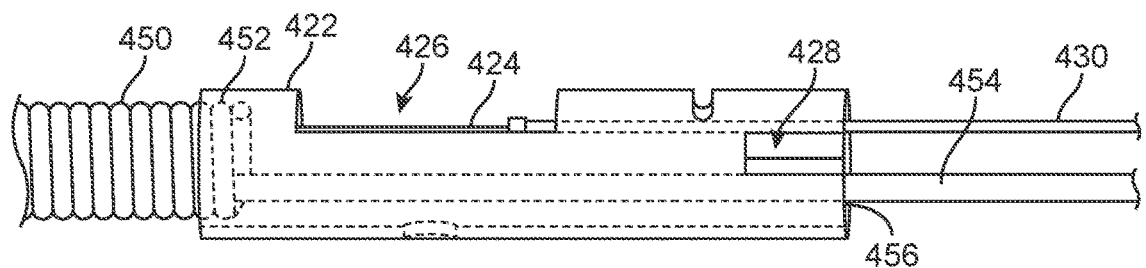
Figure 35C:
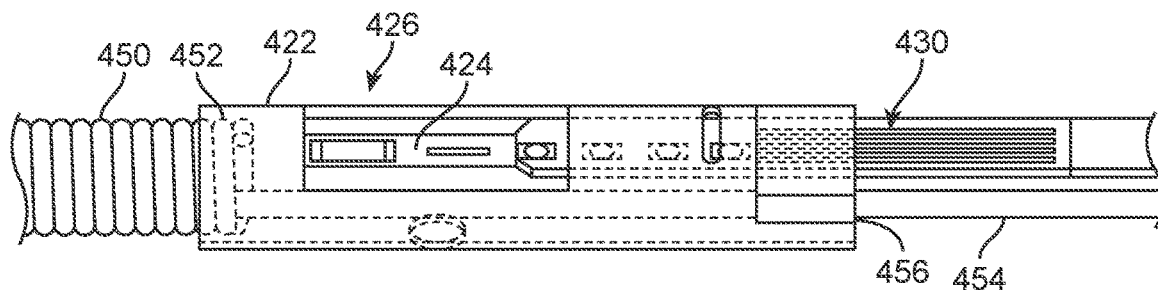
Figure 35D:
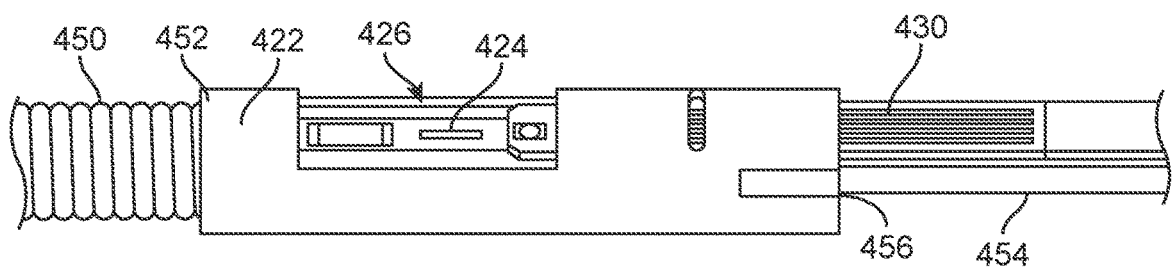

One particular method is described in the diagram 400 shown in FIG. 31 in which a number of wires, e.g., four filar flat polyester insulated copper conducting wires, may be aligned planar and adjacent to one another. The number of conducting wires may be varied, e.g., six filar, eight filar, etc., depending upon the number of discrete conductors desired. The wires may be ablated 402 at selective windows or locations along the wires which may then have a metal coat laid on of the insulation 404. Solder pads may be formed 406 at these ablated windows so that the wire forms selectively isolated pads which are available for making connections to individual wires. An example is shown in the side view of FIG. 32, which illustrates a wire assembly 410 in which selective regions of the wire 412 have been ablated through the surrounding insulation and to the underlying individual selected conducting wire. The circumferential region around each exposed window may be coated with the conductive metal coat to form metalized zones or pads 416 with regions of non-metal coated zones 414 which act as insulating regions between the metalized zones or pads 416. The wire assembly 410 may have a number of components electrically attached to a metalized zone or pad 416 for conducting signals through the wire assembly 410.

In forming the guidewire assembly, the pressure sensor packaging 420, in one variation, is shown in the perspective and side views of FIGS. 33A and 33B and may generally comprise a sensor casing 422 which may form a cylindrically shaped housing which encloses or supports the components of the pressure sensor secured within. The sensor casing 422 may define a sensing window 426 along a side surface of the casing 422 which exposes the pressure sensor 424 within to the fluid environment. A sensor core 428 may be secured within and along the sensor casing 422 which connects to a flex circuit 430 which may extend from a proximal end of the sensor casing 422 for connection to a controller or processor via one or more conductors extending through the guidewire length.

FIG. 34A illustrates a side view of one variation of a configuration for electrically connecting the sensor casing 422 components to one or more conducting wires. The sensor casing 422 is shown in a partial cross-section where the pressure sensor 424 is positioned within the sensing window 426. The flex circuit 430 is shown connected to the pressure sensor and sensor core 428 and extending proximally from the sensor casing 422. The conductive traces or wires along the flex circuit 430 may be attached directly to one or more corresponding conducting wires 440 which may extend proximally through the guidewire body (not shown for clarity) for electrical connection to a controller or processor.

FIG. 34B illustrates a side view of another variation in which the flex circuit 430 extends proximally from the sensor casing 422 but instead of being directly attached to the one or more conducting wires 440, the flex circuit 430 may be electrically connected to one or more conducting ring elements 444 which in turn are electrically connected to the one or more conducting wires. The ring elements 444 may be aligned coaxially and adjacent to one another and the number of elements 444 used may depend upon the number of electrical connections desired. The one or more conducting wires 440 may be selectively coupled electrically to a particular pad or trace on the flex circuit 430 so that each ring element 444 is electrically connected to a single pad or trace. Each ring element 444 may then be electrically coupled to a selective conducting wire 440 along an inner diameter of the ring element 444, as shown and as further described herein, leaving the remainder of the ring element 444 available for electrical connection to another conductor or component, if so desired.

FIGS. 35A to 35D show respective top, side, transparent perspective, and perspective views of another variation of the sensor casing 422 and its components to further illustrate the various configurations. As shown, the sensor casing 422 may define a longitudinal passageway 456 through the entire casing 422 to allow for passage of a guidewire core 454 therethrough. The casing 422 may further define a distal opening 452 into which a guidewire tip 450 may be positioned and secured to extend from the distal end of the casing 422 with the guidewire core 454 extending longitudinally through the casing 422 adjacent or beneath the flex circuit 430, pressure sensor 424, and sensing window 426. The sensor core 428 is shown secured within the casing 422 adjacent to the flex circuit 430 which extends proximally from the casing 422.

Figure 36:
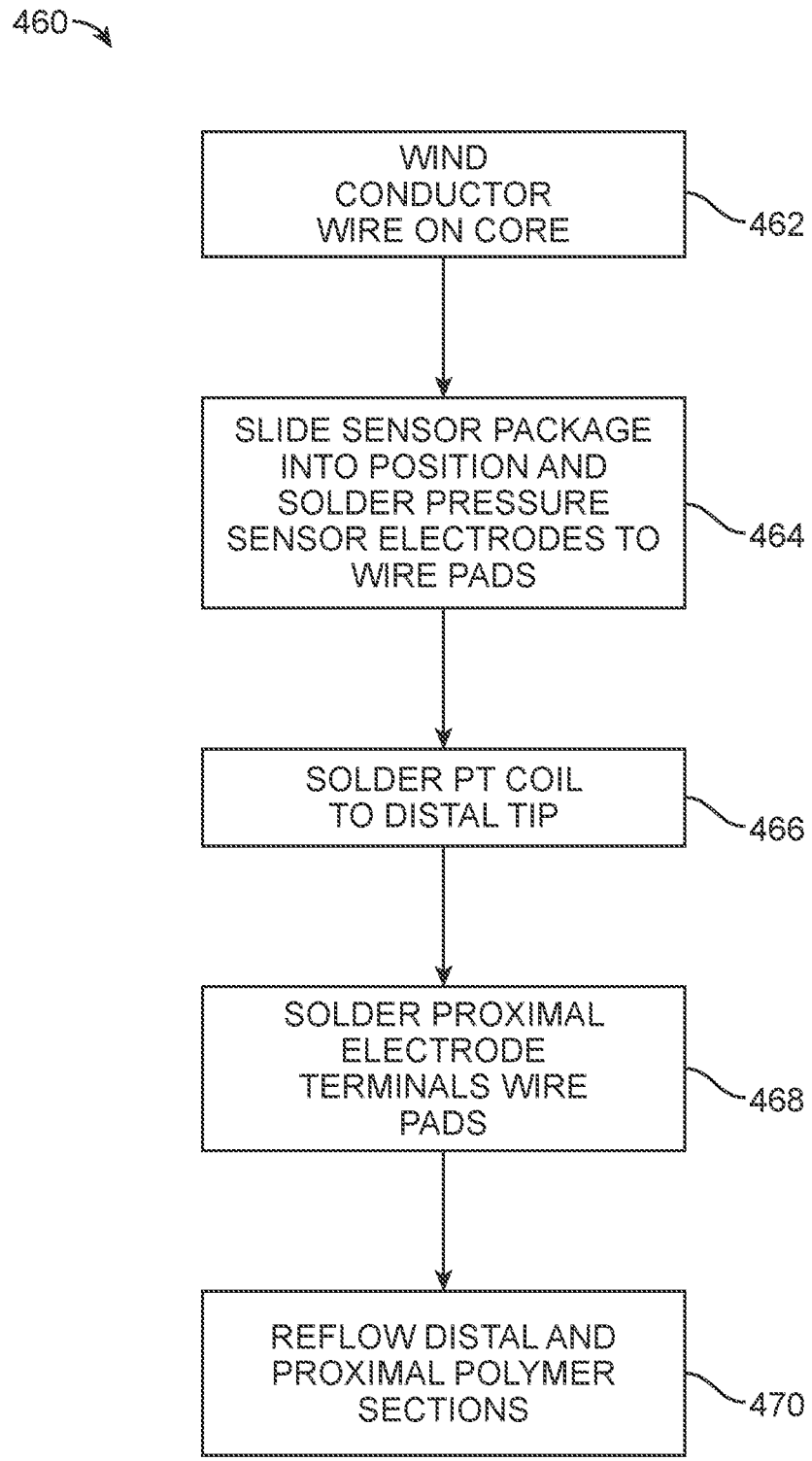
FIG. 36 shows one variation of a process flow in forming the guidewire assembly with the pressure sensor assembly.

In forming the guidewire assembly with the pressure sensor assembly, one variation of a process flow is illustrated in FIG. 36 in the flow diagram 460. In this example, a conductor wire may be wound along the guidewire core 462 distally to extend towards the sensor casing 422. The pressure sensor assembly may be slid into position along the guidewire core and the pressure sensor electrodes may be soldered onto the wire pads 464 for connection to the one or more conducting wires along the guidewire core, e.g., along the one or more ring elements 444 as described herein. The distal coil, e.g., platinum coil, may then be soldered 466 to the distal end or tip of the sensor casing 422. With the sensor casing 422 and guidewire distal tip assembled, the proximal electrode terminals, e.g., the one or more ring elements 444, may then be soldered to wire pads 468 along the guidewire. Then the exposed distal and proximal portions of the guidewire assembly may be covered by reflowing polymers 470 to encase the guidewire assembly.

Figure 37A:
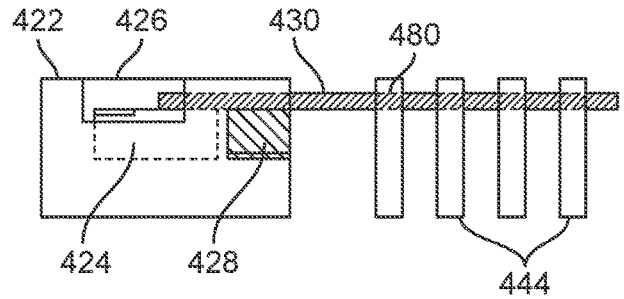
FIGS. 37A to 37E show side views of one variation of the guidewire assembly as described in the process flow of FIG. 36.

FIGS. 37A to 37E illustrate side views of one variation of the guidewire assembly as described in the process flow of FIG. 36. FIG. 37A shows a side view of a variation of pressure sensor assembly illustrating the sensor casing 422, pressure sensor 424, sensor core 428, and flex circuit 430 extending proximally from the sensor casing 422. The one or more conductive ring elements 444 are shown coaxially aligned and spaced apart from one another for electrical connection to the flex circuit 430.

Figure 37B:
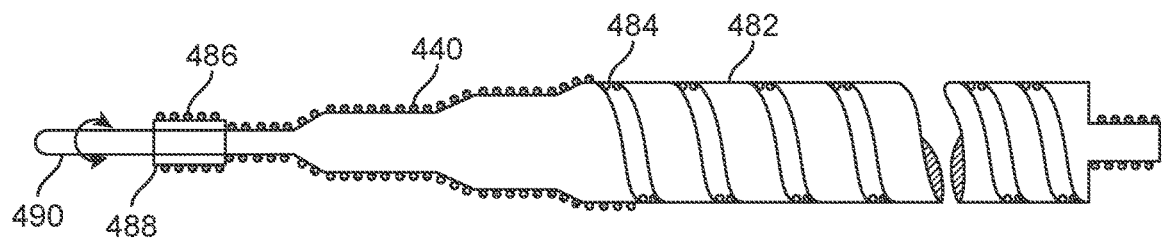
Figure 37C:
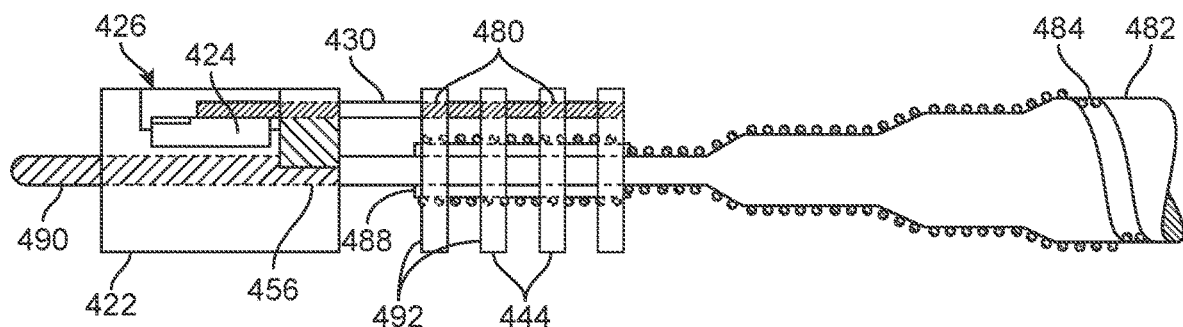

The guidewire core 482 upon which the pressure sensor assembly is to be mounted is shown in FIG. 37B. The guidewire core 482 extends longitudinally and may taper to a narrowed distal end 490. One or more conducting wires 440 may extend along the length of the guidewire core 482, e.g., in this example wound along the core 482 in a helical manner such as within a defined groove 484 along the core, to extend from the proximal end of the core 482 to the distal end 490. The one or more conducting wires 440 are shown helically wound along the remainder of the core 482 towards the distal end where the wires 440 may terminate upon an insulating tube 488 to form a conductor wire subassembly 486. The pressure sensor assembly may then be slid over the distal end 490 of the guidewire core 482 such that the core extends through the channel 456 defined through the sensor casing 422 and the one or more ring elements 444 are aligned over the conductor wire subassembly 486, as shown in FIG. 37C. Thus aligned, the one or more ring elements 444 may be electrically attached (e.g., soldered) along a portion 480 of their inner diameters to a corresponding conductive pad along the flex circuit 430 and also electrically attached (e.g., soldered) along a portion 492 of their inner diameters to a corresponding conducting wire 440 over the insulating tube 488 so that the pressure sensor 424 is electrically connected to the one or more conducting wires 440.

Figure 37D:
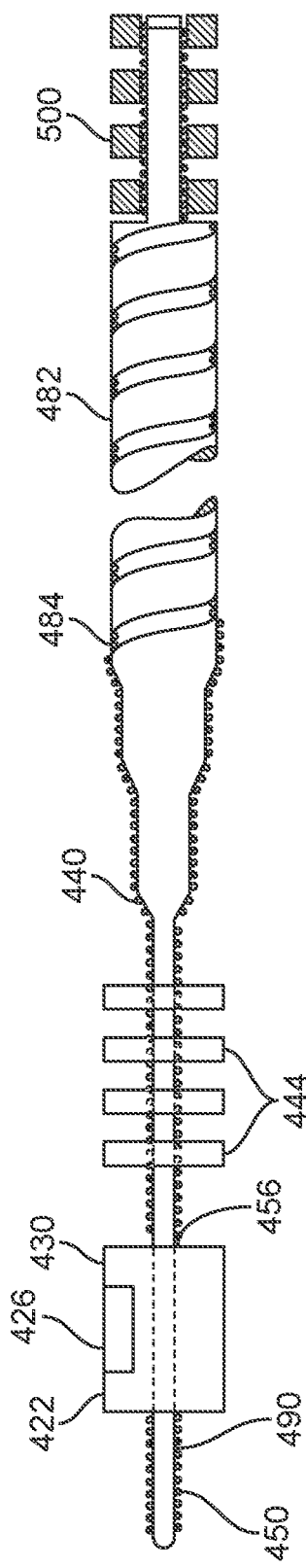
Figure 37E:
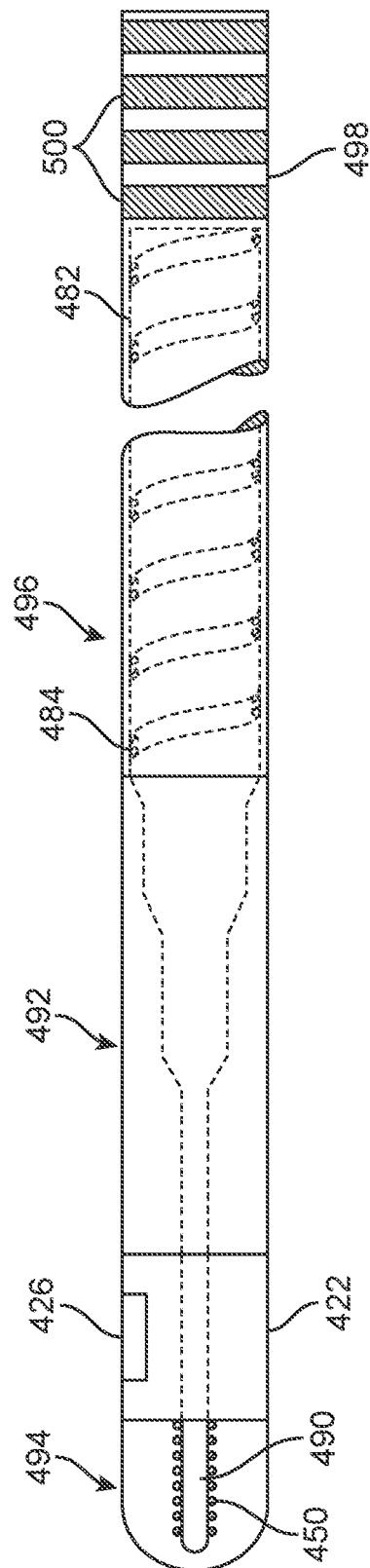

The distal coil tip 450 may be then attached to the distal end of the sensor casing 422 and the optional one or more electrodes 500 located proximally of the pressure sensor assembly may be electrically attached as well, as shown in FIG. 37D. With each of the components assembled, polymers may be reflowed or molded over the guidewire core along a central section 492, the distal coil or tip 450 along a distal section 494, and the remainder of the guidewire core along a proximal section 496 as well as the portions 498 between the electrodes 500 (if utilized), as shown in FIG. 37E. The outer diameter of the resulting guidewire may be formed to be flush to a desired outer diameter dimension.

Guidewire Conducting Ink Printing

Figure 38A:
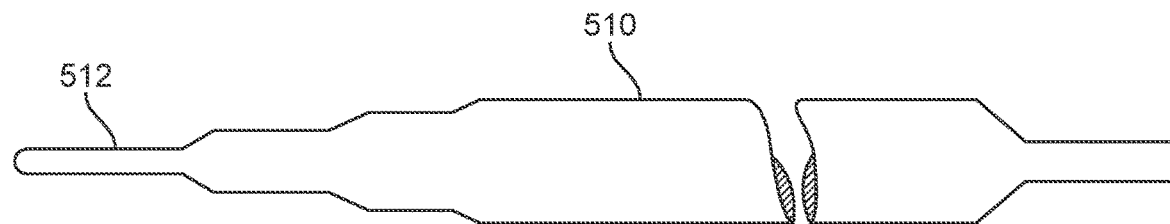
FIGS. 38A to 38C show side views of a guidewire assembly having conductive ink printed upon a polymer substrate to form a subassembly.
Figure 38B:
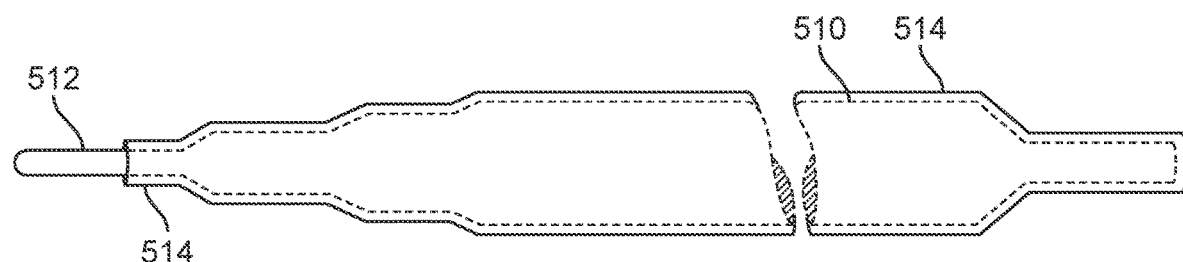
Figure 38C:
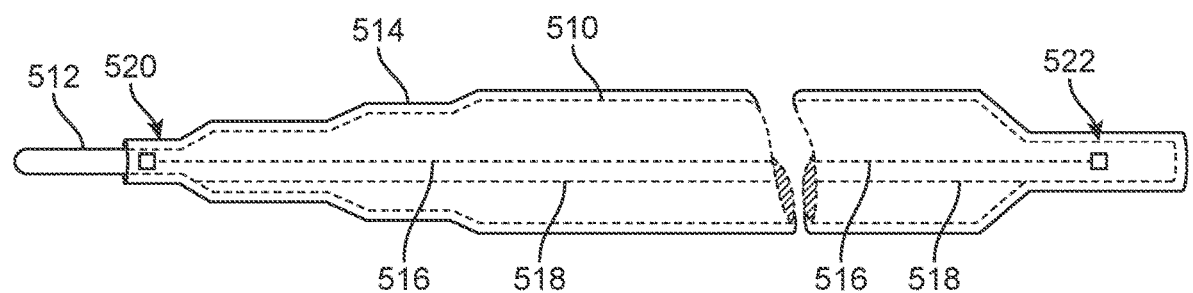

In yet another variation for electrically coupling elements within or along a guidewire, FIGS. 38A to 38C show side views of a guidewire assembly having conductive ink printed upon a polymer substrate to form a subassembly for carrying signals from one end to the other end of the guidewire or catheter. Using conductive traces directly upon the device substrate and then insulating the traces by a dielectric material eliminates the need to have conducting wires and associated processing and handling of the same.

FIG. 38A shows a side view of a guidewire core 510 which tapers to a distal end 512. A polymer layer 514 (e.g., PET, PTFE, etc.) may be coated over the guidewire core 510 such as via heat shrink, as shown in FIG. 38B, to provide an insulating substrate. The polymer layer 514 may be coated or laid upon the entirety of the guidewire core 510 or a portion of the distal end 512 may remain uncoated for securement of the pressure sensor assembly. The one or more conductive traces 516, 518 (e.g., nano silver, nano gold, nano copper, etc.) may then be printed directly upon the polymer layer 514 such that the traces 516, 518 extend from one or more corresponding distal pads 520 to one or more corresponding proximal pads 522.

One such printing technique uses Aerosol Jet technology which is a non-contact printing technique capable of patterning a wide variety of electronic and polymeric materials at the micrometer size scale. In the jetting process, a liquid ink is aerosolized and the mist is aerodynamically focused to a micron-scale point on the target substrate. The large standoff distance between the Aerosol Jet tools printing tip and the substrate (e.g., greater than mm) enables the additional capability of manipulating jetted particles during their flight to the substrate. With robotic manipulation of the print head and target substrate, the 3D features can be fabricated in nearly any orientation including the fabrication of hollow structures such as microbubbles. It is also feasible to co-deposit electronic and polymeric materials making it possible to fabricate hybrid electronics. In this case the polymeric materials serve as the mechanical support for printed metal conductors and other electronic materials.

Figure 39A:
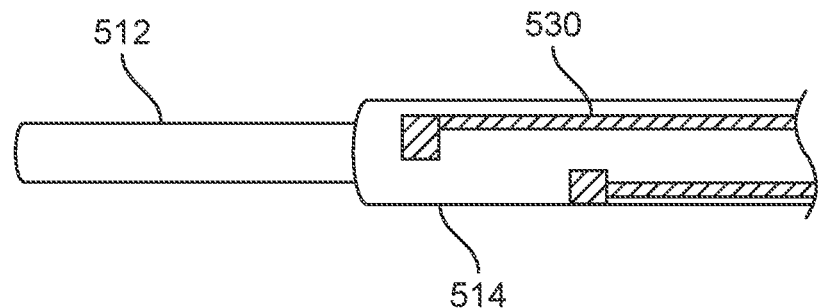
FIGS. 39A to 39C show different trace patterns for the conductive traces.
Figure 39B:
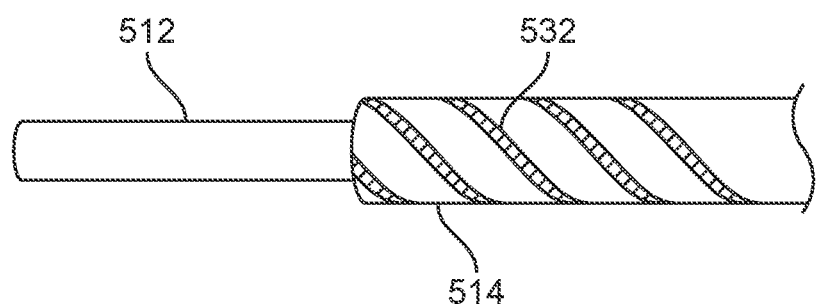
Figure 39C:
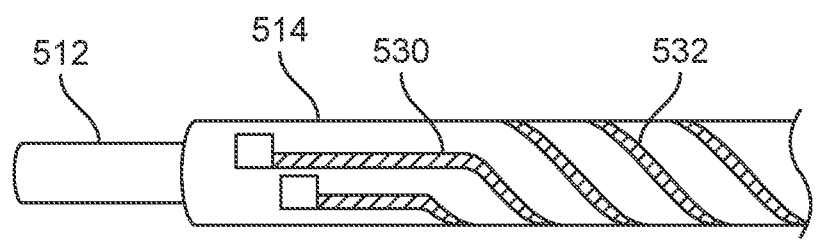

Because these one or more conductive traces are printed directly upon the polymer layer 514, they may be configured in a number of different patterns. One example is shown in FIG. 39A which illustrates how the traces 530 may be printed in a straight pattern along the polymer layer 514. FIG. 39B shows another example where the traces 532 may be printed in a helical pattern while FIG. 39C shows yet another example where a combination of straight 530 and helical 532 patterns may be combined in a single trace. These trace patterns are intended to be illustrative of the different types of configurations and any number of other patterns may be utilized alone or in combination with one another.

Once the one or more conductive traces have been printed upon the polymer layer, the traces may then be insulated. One variation for insulating the traces may involve masking the ends of the traces that will need to remain exposed to form pads for electrical connections and then depositing another layer of polymer upon the conductive traces. For instance, another heat shrink tubing or layer may be used or another layer of polymer (such as PTFE, paralyne, etc.) may be deposited upon the exposed conductive traces using, e.g., physical vapor deposition, dip coating, etc.).

In yet another variation, a conductive coating can be applied over the dielectric coating either by a bulk metallization process such as physical vapor deposition (PVD), or by electro plating, electroless plating, printing a wider metal layer using conductive inks on top of the dielectric layer, etc. Such a metal layer can provide EM shielding and thus eliminate or reduce noise and increase system signal to noise ratio (SNR).

Figure 40A:
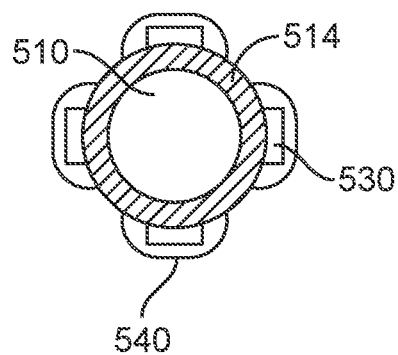
FIGS. 40A and 40B show cross-section and side views of a guidewire core and conductive traces with the overlaid insulating layer.
Figure 40B:
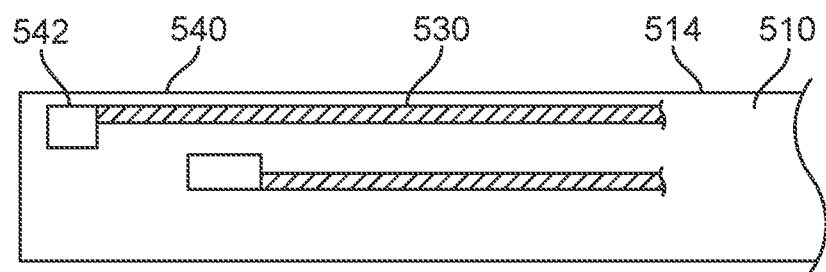

Another variation for insulating the traces may involve printing a dielectric polymer directly upon the conductive traces using polymer inks. The resulting cross-section of the guidewire core 510 and conductive traces 530 with the overlaid insulating layer 540 is shown in FIG. 40A. In the case of using polymer inks to directly print upon the conductive traces, the printing process may be used to selectively print the polymer ink to create the insulating layer 540 while exposing portions of the conductive traces to form conductive pads 542 for electrical coupling to components, as shown in FIG. 40B.

Figure 41A:
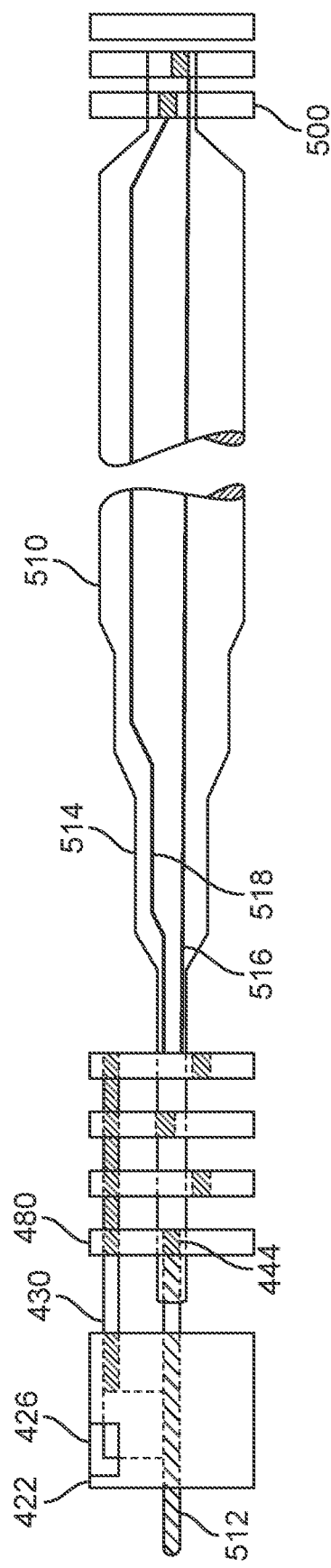
FIGS. 41A and 41B show side views of the resulting guidewire core and polymer layer coupled with the pressure sensor assembly.
Figure 41B:
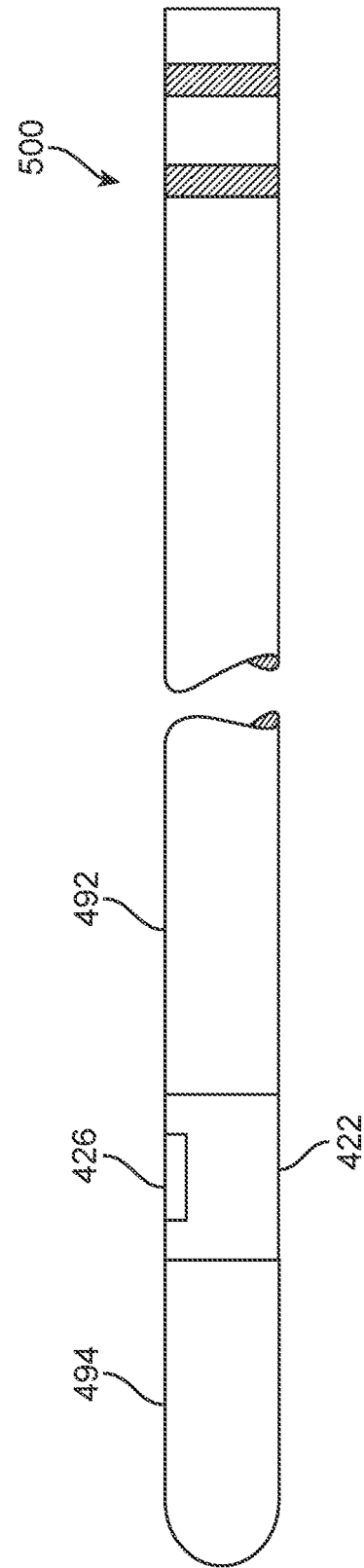

Regardless of which method is used, the resulting guidewire core 510 and polymer layer 514 may be coupled with the pressure sensor assembly, as shown in FIG. 41A. The one or more ring elements 444 may be electrically coupled along portions of their inner diameter to a corresponding pad exposed along the flex circuit 430, as described herein, and a second portion along the one or more ring elements 444 may be electrically coupled to a corresponding pad of the conductive traces disposed upon the polymer layer 514 to electrically couple the pressure sensor assembly (or any other component). The distal coil tip may then be attached to the distal end of the sensor casing 422 and the polymers may be reflowed or molded over the guidewire core along the central section 492, the distal coil or tip 450 along the distal section 494, and the remainder of the guidewire core along the proximal section 496 as well as the portions 498 between the electrodes 500 (if utilized), as shown in FIG. 41B.

Another variation of the assembly method is shown in FIGS. 42A and 42B which illustrate side views of the polymer layer 514 formed separately prior to being disposed upon the guidewire core. The conductive traces 554, 556 may be printed directly upon the outer layer of the polymer 514 along with their corresponding exposed pads 550, 558 and 552, 560 extending over the length of the polymer layer 514, as shown in FIG. 42A. The insulative layer may be likewise printed directly upon the conductive traces 554, 556, as previously described. With the pre-printed polymer layer 514, the guidewire core 512 may be inserted into the polymer layer 514 and bonded with any number of suitable adhesives, e.g., cyanoacrylate, etc. The pressure sensor assembly may then be secured to the guidewire core 512 and the flex circuit 430 may be electrically coupled directly to the exposed pads 550, 552 at attachments 562 to complete the electrical connection, as shown in FIG. 42B.

In yet another variation for printing conductive traces, FIGS. 43A to 43D show a variation in which a polymer tube 572 may be disposed upon a guidewire core 570 and one or more conductive traces 574 may be printed upon the outer layer of the tube 572, as previously described. FIGS. 43A and 43B show side and end views of the conductive traces 574 printed upon the outer surface of the tube 572. Insulative layers 576 may then be printed directly over the conductive traces 574, as previously described, while leaving selective regions 578A, 578B, 578C of the conductive traces 574 exposed, as shown in FIG. 43C.

Conductive ink may then be used to print circular rings 580A, 580B, 580C upon the polymer tube 572 such that a ring coincides with an exposed region 578A, 578B, 578C of the conductive traces 574, as shown in FIG. 43D, so that the pressure sensor assembly flex circuit 430, or any other component, may be electrically coupled to the conductive traces 574 via connection to the circular rings 580A, 580B, 580C. Because the circular rings 580A, 580B, 580C are printed circumferentially around the tube 572, the exposed regions 578A, 578B, 578C may be off set longitudinally from one another to allow for the ring to be printed around the entire tube 572 circumference. Also, there is preferably adequate longitudinal spacing between the exposed regions 578A, 578B, 578C to allow for the rings 580A, 580B, 580C to be printed coaxially relative to one another without interference. In other variations, partial circumferential rings may be printed than full circumferential rings.

Figure 44A:
FIGS. 44A to 44E show yet another variation for creating conductive traces upon a guidewire core.
Figure 44B:
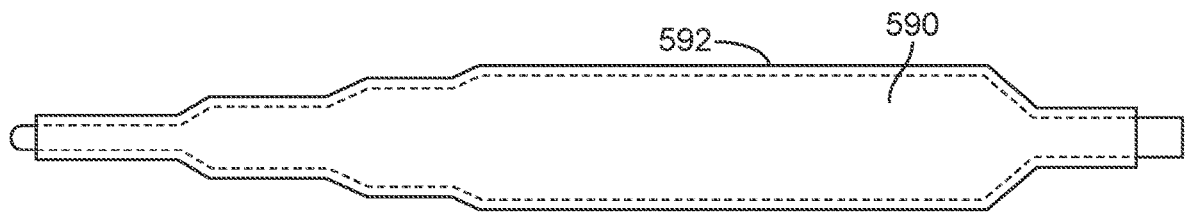
Figure 44C:
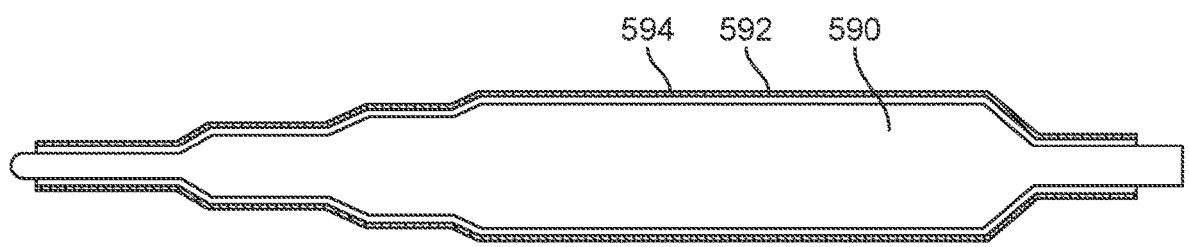

Yet another variation for creating conductive traces is shown in FIGS. 44A to 44E. In this variation, a guidewire core 590, as shown in FIG. 44A, may have a first insulative polymer layer 592 (e.g., PARYLENE (Specialty Coating Systems, Inc., Indianapolis, IN), TEFLON (E. I. Du Pont De Nemours, Wilmington, DE), polyimide, etc.) disposed upon an outer surface of the guidewire core 590, as shown in FIG. 44B. A second conductive polymer layer 594 (gold, silver, copper, etc.) having a conductive material may then be coated upon the first polymer layer 592, as shown in FIG. 44C, using any number of processes such as, e.g., electroless deposition, physical vapor deposition, etc. The thickness of the conducting layer is dependent on the application and is often determined considering both electrical requirements (current carrying capacity) and mechanical requirements of the device (e.g. stiffness). This second conductive layer 594 may be separated into discrete conductive elements using, e.g., laser micro machining, photochemical etching, etc.

The entire assembly can then be insulated using dielectric insulative polymer either in the form of a coating or heat shrink (e.g. Teflon, PET, etc.) depending on the application. Depending on the application several discrete conducting elements can be formed. Also depending on the application various connecting terminal size and shapes can be formed at either ends to facilitate connecting to the discrete conducting elements so formed. Such a construction technique helps achieve several discrete conducting elements directly on the device thereby eliminating the need to remove material to accommodate separate conducing wires or make the device hollow to accommodate conducting wires or elements. Therefore, the intended device performance is greatly enhanced and manufacturing costs are reduced.

Figure 44D:
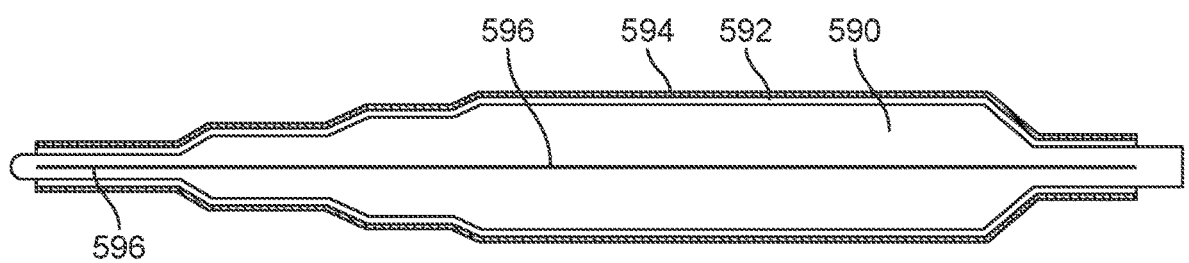
Figure 44E:
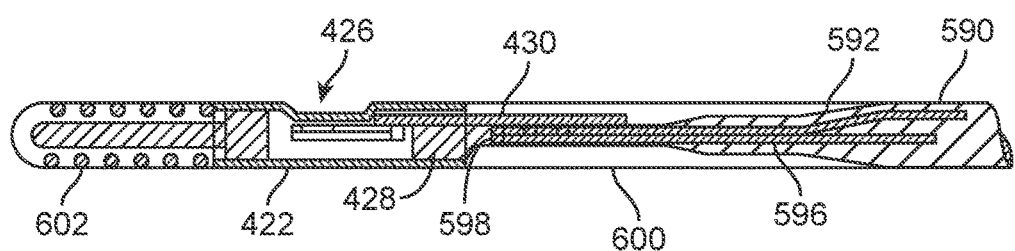

The example shown in FIG. 44D illustrates how the second conductive layer 594 may be removed to leave one or more conductive traces 596 along the length of the guidewire core. Although this example illustrates a single trace 596, any number of traces and/or pads and varying configurations may be utilized. The completed assembly may be used to connect with the pressure sensor assembly and electrically connected 598 to the flex circuit 430. The proximal and distal portions 600, 602 of the guidewire may be coated or covered with a polymer layer, as previously described to form a flush outer surface.

It is intended that any of the various manufacturing and assembly processes described herein for the sensor die and/or electrode assembly may be combined in any combination as practicable. For instance, any of the assembly methods and apparatus for integrating the electrode assembly along a guidewire may be applied in combination with any of the assembly methods and apparatus for integrating the sensor along the guidewire as well. Hence, each of the variations described may be utilized alone or in any number of combinations as well.

What is claimed is:

1. A guidewire assembly comprising:
   a guidewire core having a distal end side that includes a smaller-diameter portion and a larger-diameter portion, the larger-diameter portion being located proximally with respect to the smaller-diameter portion,
   a first insulative layer that is provided over the smaller-diameter portion and the larger-diameter portion,
   a plurality of conductive traces that are each arranged on the first insulative layer and extend at least from the smaller-diameter portion to the larger-diameter portion,
   a second insulative layer provided over the first insulative layer and the plurality of conductive traces; and
   a sensor disposed on the smaller-diameter portion, wherein the sensor is electrically connected to the plurality of conductive traces at the distal end side, and at least one of the plurality of conductive traces includes a linear portion that extends along a lengthwise axis direction of the guidewire core and a spiral portion that is arranged spirally around the guidewire core.

2. The guidewire assembly of claim 1, wherein the spiral portion is located proximally on the guidewire core relative to the linear portion.

3. The guidewire assembly of claim 1, wherein each of the plurality of conductive traces includes a linear portion that extends along the lengthwise axis direction of the guidewire core.

4. The guidewire assembly of claim 3, wherein the linear portions of all of the plurality of conductive traces are arranged parallel to each other.

5. The guidewire assembly of claim 1, wherein the linear portion extends continuously to the spiral portion.

6. The guidewire assembly of claim 1, wherein the plurality of conductive traces extend from the smaller-diameter portion to a proximal end side of the guidewire core.

7. The guidewire assembly of claim 1, wherein the linear portion is provided on the smaller-diameter portion.

8. The guidewire assembly of claim 1, wherein the spiral portion extends from the smaller-diameter portion to the larger-diameter portion.

* * * * *